(12) United States Patent
Usui et al.

(10) Patent No.: US 7,632,639 B2
(45) Date of Patent: Dec. 15, 2009

(54) SIGNAL AMPLIFICATION METHOD FOR DETECTING MUTATED GENE

(75) Inventors: Mitsugu Usui, Yokohama (JP); Toshihiko Fujikawa, Kawasaki (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 10/546,593

(22) PCT Filed: Feb. 20, 2004

(86) PCT No.: PCT/JP2004/002007

§ 371 (c)(1),
(2), (4) Date: Aug. 19, 2005

(87) PCT Pub. No.: WO2004/074480

PCT Pub. Date: Sep. 2, 2004

(65) Prior Publication Data

US 2006/0210983 A1     Sep. 21, 2006

(30) Foreign Application Priority Data

Feb. 21, 2003    (JP) ............................. 2003-044859

(51) Int. Cl.
C12Q 1/68 (2006.01)
C07H 21/04 (2006.01)
(52) U.S. Cl. .......................... 435/6; 536/24.3
(58) Field of Classification Search ............... None
See application file for complete search history.

(56) References Cited

U.S. PATENT DOCUMENTS

| 4,988,617 | A | 1/1991 | Landegren et al. |
| 5,985,557 | A | 11/1999 | Prudent et al. |
| 6,261,846 | B1 | 7/2001 | Usui |
| 2002/0150921 | A1 | 10/2002 | Barany et al. |
| 2003/0008294 | A1 | 1/2003 | Usui et al. |
| 2003/0022182 | A1 | 1/2003 | Barany et al. |
| 2003/0175689 | A1 | 9/2003 | Usui et al. |

FOREIGN PATENT DOCUMENTS

| AU | 747848 | 10/2001 |
| AU | 200144583 | 10/2001 |

(Continued)

OTHER PUBLICATIONS

DA Nickerson, et al., "Automated DNA diagnostics using an ELISA-based oligonucleotide litigate assay" *PNAS*, vol. 87, pp. 8923-8927, 1990.

(Continued)

*Primary Examiner*—Young J Kim
*Assistant Examiner*—Samuel Woolwine
(74) *Attorney, Agent, or Firm*—Wenderoth, Lind & Ponack, L.L.P.

(57) ABSTRACT

There is provided a signal amplification method for detecting a mutated gene, which can increase the detection sensitivity of mutated genes on a DNA chip according to the PALSAR method, can establish efficient signal amplification and can establish simple detection by contriving design of oligonucleotide probes for use in the PALSAR method. The signal amplification method comprises a ligation reaction with a DNA ligase and a self-assembly reaction which forms a double-stranded self-assembly substance having a regular higher-order structure of oligonucleotides, wherein the detection sensitivity of the mutated gene on a DNA chip is improved.

12 Claims, 21 Drawing Sheets

FOREIGN PATENT DOCUMENTS

| | | |
|---|---|---|
| CN | 1388831 | 1/2003 |
| EP | 1 002 877 | 5/2000 |
| EP | 1 188 841 | 3/2002 |
| EP | 1 229 131 | 8/2002 |
| JP | 2000-201687 | 7/2000 |
| JP | 3267576 | 7/2000 |
| JP | 2001-553955 | 3/2001 |
| JP | 2002-522547 | 8/2001 |
| JP | 2001-519648 | 10/2001 |
| JP | 3267576 | 1/2002 |
| JP | 3310662 | 5/2002 |
| WO | 92/20702 | 11/1992 |
| WO | 95/21271 | 8/1995 |
| WO | 97/31256 | 8/1997 |
| WO | 00/04192 | 1/2000 |
| WO | 01/75157 | 10/2001 |
| WO | 02/18642 | 3/2002 |
| WO | 03/029441 | 4/2003 |
| WO | 03/040367 | 5/2003 |

OTHER PUBLICATIONS

X Chen and P Kwok, "Template-directed dye-terminator incorporation (TDI) assay: a homogeneous DNA diagnostic method based on fluorescence resonance energy transfer", *Nucleic Acids Research*, vol. 25, No. 2, pp. 347-353, 1997.

A Koshkin, et al., "LNA (locked nucleic acids): synthesis of the adenine, cytosine, guanine, 5-methylcytosine, thymine and uracil bicyclonucleoside monomers, oligomerisation, and unprecedented nucleic acid recognition", *Tetrahedron*, vol. 54, pp. 3607-3630, 1998.

A Koskin, et al., "LNA (locked nucleic acid): an RNA mimic forming exceedingly stable LNA:LNA duplexes", *J. Am. Chem. Soc.*, vol. 120, pp. 13252-13253, 1998.

C Wahlestedt, et al., "Potent and nontoxic antisense oligonucleotides containing locked nucleic acids", *PNAS*, vol. 97, pp. 5633-5638, 2000.

Spot positions of Capture Probes

| CP-2-T | CP-2-C | CP-8-C | CP-8-T |
| CP-3-C | CP-3-T | CP-9-G | CP-9-C |
| CP-4-G | CP-4-A | CP-10-C | CP-10-G |
| CP-5-C | CP-5-T | CP-1-G | CP-1-A |
| CP-6-A | CP-6-G | CP-11-G | CP-11-T |
| CP-7-A | CP-7-G | CP-12-A | CP-12-T |

SIGNAL AMPLIFICATION METHOD FOR DETECTING MUTATED GENE

This application is a U.S. national stage of International Application No. PCT/JP2004/002007 filed Feb. 20, 2004.

TECHNICAL FIELD

The present invention relates to a signal amplification method using a ligation reaction and a self-assembly reaction for forming a self-assembly substance, which can improve the detection sensitivity of a mutated gene on a DNA chip, a DNA microarray, a microwell, or a spherical bead (in the present invention, a DNA chip, a DNA microarray, a microwell, or a spherical bead is generically referred to as "a DNA chip").

BACKGROUND ART

Conventional gene mutation detection uses a variety of methods such as an OLA (oligonucleotide ligation assay) method in which oligonucleotides are bound to a target and ligated using a DNA ligase (for example, see U.S. Pat. No. 4,988,617 and D. Nickerson, Proc. Natl. Acad. Sci., vol. 87, pp. 8923-8927 (1990)), a TDI (template-directed dye-terminator incorporation) method in which labeled ddNTP is used for single base elongation (for example, see Chen X et al., Nucleic Acids Research, vol. 25, No. 2, pp. 347-353 (1997)), and an invader method (for example, see U.S. Pat. No. 5,985, 557). However, the conventional methods have problems of multiplex, cost, versatility, or the like.

There is known a conventional technique which comprises the steps of fixing a large number of DNA probes at a high density on a support such as a slide glass with the surface specially treated, and hybridizing a labeled target or a signal detecting probe to detect signals. However, this technique has the problem that its sensitivity is as low as one tenth of the sensitivity of a conventional Southern blotting method (for example, see Masaaki Muramatsu et al., DNA Microarrays and Current PCR Techniques, Shujunsha Co., Ltd. 85-86, 2000) and that the reaction time is relatively long.

In light of the above problems, the present inventors have proposed a novel isothermal nucleic acid amplification method without using any enzyme (for example, see Japanese Patent No. 3267576). This method utilizes a pair of oligonucleotides each comprising three regions (Honeycomb Probe, referred to as "HCP" hereinafter) in which the three respective regions of a first HCP and a second HCP are designed to be composed of base sequences complementary to each other so that only one region of the first HCP may be hybridized with one region of the second HCP when the both HCPs are reacted. This design makes it possible for a plurality of pairs of the HCPs to hybridize to each other and form an assembly substance by a self-assembly reaction of the HCPs when the pairs of HCPs are reacted (this method for the formation of an assembly substance by the self-assembly reaction is referred to as a PALSAR method hereinafter).

DISCLOSURE OF THE INVENTION

In view of the present state of the prior art described above, the present inventors have made active investigations in order to increase the detection sensitivity of mutated genes by the PALSAR method and finally have made the present invention.

It is an object of the present invention to provide a signal amplification method for detecting a mutated gene, which can increase the detection sensitivity of a mutated gene on a DNA chip according to the PALSAR method, can establish efficient signal amplification and can establish simple detection by contriving design of oligonucleotide probes for use in the PALSAR method.

In order to solve the problem, a first aspect of a signal amplification method for detecting a mutated gene according to the present invention comprises a ligation reaction with a DNA ligase and a self-assembly reaction which forms a double-stranded self-assembly substance having a regular higher-order structure of oligonucleotides, wherein the detection sensitivity of the mutated gene on a DNA chip is improved.

A second aspect of a signal amplification method for detecting a mutated gene according to the present invention comprises:

a first step for hybridizing a capture probe and a first probe to a target DNA;

a second step for joining the capture probe and the first probe by a ligation reaction with a DNA ligase when the target DNA has a mutation site that is complementary to the capture probe;

a third step for removing the target DNA; and a fourth step for adding a plurality of oligonucleotide probes to form a self-assembly substance by a self-assembly reaction of the oligonucleotide probes so that signal amplification is achieved, wherein the base sequences of the capture probe and the first probe are constructed such that, in the first step, the capture probe and the first probe are annealed to the target DNA in the state where a end of the capture probe places at the mutation site of the target DNA and the end is adjacent to the first probe, and at least one of the plurality of oligonucleotide probes has a region complementary to the first probe. This signal amplification method can increase the detection sensitivity of a mutated gene on a DNA chip. In the first step, the capture probe and the first probe may be bound to the target DNA in any order. For example, the capture probe and the first probe may be simultaneously bound to the target DNA; after the capture probe is bound to the target DNA, the first probe may be bound to the target DNA; or after the first probe is bound to the target DNA, the capture probe may be bound to the target DNA.

In a preferred mode, a base sequence of the oligonucleotide probe for use in the self-assembly reaction is made previously complementary to a base sequence of the first probe in advance.

In one aspect, the above self-assembly reaction may comprise the steps of:

providing a plurality of pairs of oligonucleotide probes (referred to as "HCPs" with respect to the present invention) comprising n (n≧3) regions, each region of a first probe of the pair of probes being complementary to each region of a second probe of the pair of probes;

and hybridizing the pairs of oligonucleotide probes such that the first probes and the second probes cross each other in alternation, wherein the oligonucleotide probes are self-assembled to form the double-stranded self-assembly substance. In case of detecting one kind of mutated gene, one of the pair of HCPs is preferably constructed so as to serve as the first probe.

In another aspect, the above self-assembly reaction may comprise the steps of:

providing a first group and a second group, the first group including a plurality of pairs of dimer-forming probes containing a pair of an oligonucleotide No. 1 and an oligonucleotide No. 2, each oligonucleotide having three regions of a 3' side region, a mid-region and a 5' side region, in which the mid-regions thereof have base sequence complementary to each other to form a dimer probe, and the 3' side regions and the 5' side regions thereof have base sequences not complementary to each other, and the second group including a plurality of pairs of cross-linking probes containing a pair of an oligonucleotide No. 3 and an oligonucleotide No. 4, each oligonucleotide having two regions of a 3' side region and a 5' side region, in which the 3' side regions and the 5' side regions thereof have base sequences not complementary to each other, and the pairs of the cross-linking probes having base sequences capable of cross-linking the dimer probes formed from the dimer-forming probes; and hybridizing the probes, wherein the oligonucleotides are self-assembled to form the self-assembly substance. The pair of the dimer-forming probes and the pair of the crosslinking probes are preferably constructed such that either thereof, more preferably, one of the pair of the dimer-forming probes serves as the first probe.

The base sequences of the above probes may be complementary to each other in the following respective pairs:

the 3' side region of the oligonucleotide No. 1 in the first group and the 3' side region of the oligonucleotide No. 3 in the second group;

the 5' side region of the oligonucleotide No. 2 in the first group and the 5' side region of the oligonucleotide No. 4 in the second group;

the 3' side region of the oligonucleotide No. 4 in the second group and the 3' side region of the oligonucleotide No. 2 in the first group; and the 5' side region of the oligonucleotide No. 3 in the second group and the 5' side region of the oligonucleotide No. 1 in the first group.

Also, the base sequences of the probes may be complementary to each other in the following respective pairs:

the 3' side region of the oligonucleotide No. 1 in the first group and the 3' side region of the oligonucleotide No. 3 in the second group;

the 5' side region of the oligonucleotide No. 2 in the first group and the 5' side region of the oligonucleotide No. 3 in the second group;

the 3' side region of the oligonucleotide No. 2 in the first group and the 3' side region of the oligonucleotide No. 4 in the second group; and the 5' side region of the oligonucleotide No. 1 in the first group and the 5' side region of the oligonucleotide No. 4 in the second group.

The target DNA may be single-stranded DNA or double-stranded DNA. In the signal amplification method, for the target DNA, the single-stranded DNA is directly employed, while the double-stranded DNA may be also employed by separation of the two strands. For example, there may be used DNA amplified by a gene amplification method (such as a PCR method or an LCR method) using DNA as template. When the target gene is RNA, DNA amplified by a gene amplification method (such as an RT-PCR method) using RNA as template may be used according to the present invention.

In a preferred mode, the DNA chip has a support to which a capture probe for capturing the target DNA is bound. The support is preferably a microplate type, a slide glass type, a particle type, or an electroconductive substrate type. The microplate type or particle type support may be made of plastics such as polystyrene. Materials such as glass and plastics may be used for the slide glass type support. A gold electrode, an ITO (indium oxide) electrode or the like may be used for the electroconductive substrate type support.

There may be hybridized a labeled probe which is in advance labeled with an enzyme of color generation type, an enzyme of a luminescence generation type, a radioisotope, or the like, with the self-assembly substance, so that the presence of the self-assembly substance can be detected.

The presence of the self-assembly substance may be detected by:

adding a fluorescent substance capable of binding to a nucleic acid to the self-assembly substance; and measuring a photochemical change of the fluorescent substance.

The presence of the self-assembly substance may be detected by:

labeling previously the oligonucleotide for forming the self-assembly substance with a fluorescent substance; and measuring a photochemical change of the fluorescent substance.

The presence of the self-assembly substance may be detected by:

labeling in advance the oligonucleotide for forming the self-assembly substance with a radioisotope; and detecting the radioisotope.

The presence of the self-assembly substance may be detected by:

labeling in advance the oligonucleotide for forming the self-assembly substance with an enzyme of color generation type or an enzyme of luminescence generation type; and measuring a photochemical change due to the enzyme.

The above oligonucleotides may be comprised of at least one base selected from the group consisting of DNA, RNA, PNA, and LNA.

BEST MODE FOR CARRYING OUT THE INVENTION

The embodiments of the present invention are described below with reference to the attached drawings. It should be understood that the embodiments described herein are merely exemplary and that many variations and modifications may be made without departing from the spirit and scope of the present invention.

Figure 1:
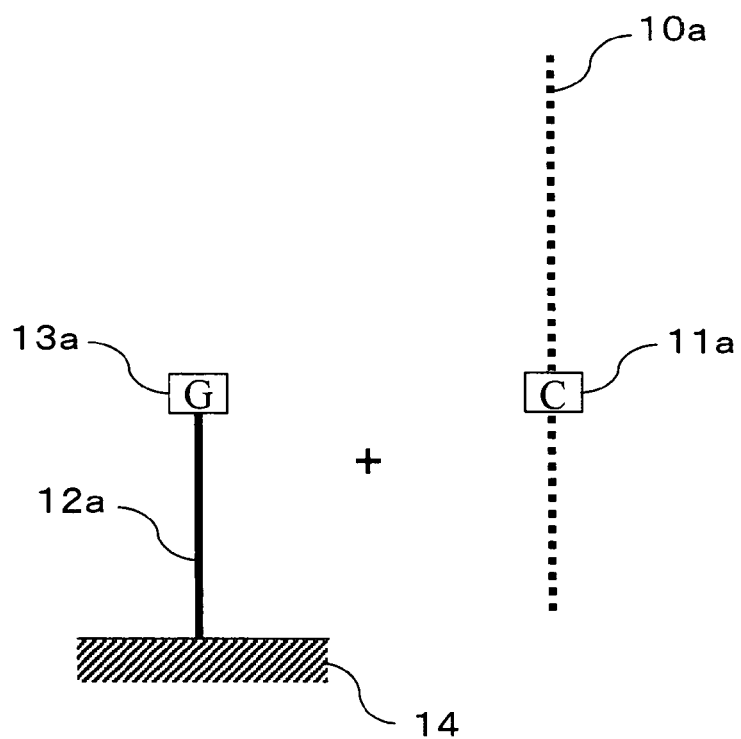
FIG. 1 is a schematic diagram showing in principle the step 100 in the first to fourth embodiments of order of steps of the signal amplification method of the present invention.
Figure 2:
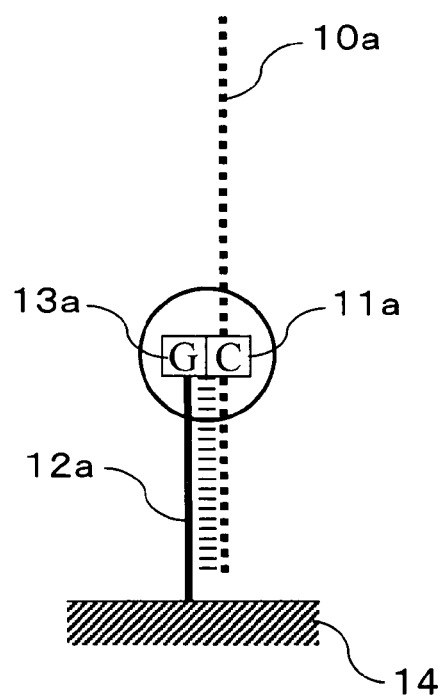
FIG. 2 is a schematic diagram showing in principle the step 102 in the first to fourth embodiments of order of steps of the signal amplification method of the present invention.
Figure 3:
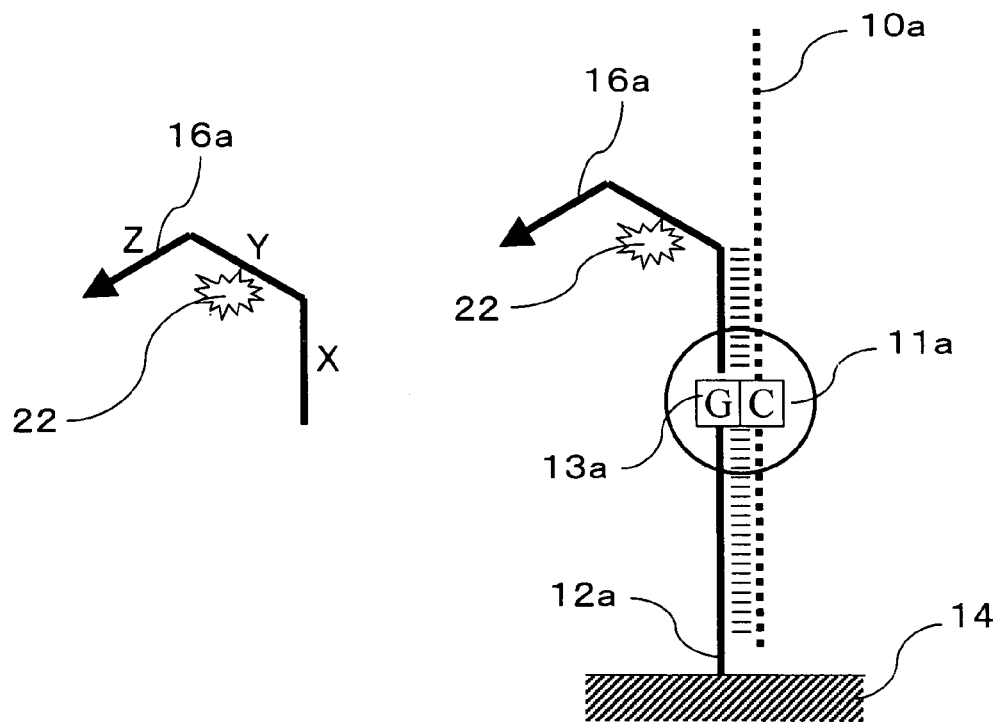
FIG. 3 is a schematic diagram showing in principle the step 110 in the first embodiment of order of steps of the signal amplification method of the present invention.

FIGS. 1 to 6 are schematic diagrams showing in principle the first embodiment of order of steps of the signal amplification method according to the present invention. In the first embodiment, a mutation site 11a of a target DNA 10a is complementary to an end 13a of a capture probe 12a. The first embodiment of the signal amplification method uses the PALSAR method in which a pair of oligonucleotide probes is used. The pair of oligonucleotide probes includes three complementary pairs of regions and can self-assemble by themselves to form an assembly. Specifically, the pair of oligonucleotide probes comprises a pair of HCPs: HCP-1 (5'-X-Y-Z-3') 16a and HCP-2 (5'-X'-Y'-Z'-3') 18a. Referring to FIG. 3, the pair of the HCPs 16a and 18a is in advance labeled with a fluorescent substance 22, and the HCP-1 16a is constructed such that it has a region complementary to the target DNA 10a and hybridizes with the target DNA 10a with being adjacent to the capture probe 12a.

Referring to FIG. 1, the capture probe 12a is bound to a support 14, and the target DNA 10a is added thereto (step 100). The capture probe 12a has a region complementary to the target DNA 10a and the end 13a thereof is placed at the gene mutation site 11a of the target DNA 10a. Referring to FIG. 2, the target DNA 10a is then captured (step 102). Thereafter, referring to FIG. 3, the HCP-1 16a is bound to the target DNA 10a with the HCP-1 16a adjoining the capture probe 12a (step 110). The HCP-1 16a has a region complementary to the target DNA 10a and is one of the HCPs, wherein the HCPs are labeled with the fluorescent substance 22 and can self-assemble by themselves to form an assembly.

Figure 4:
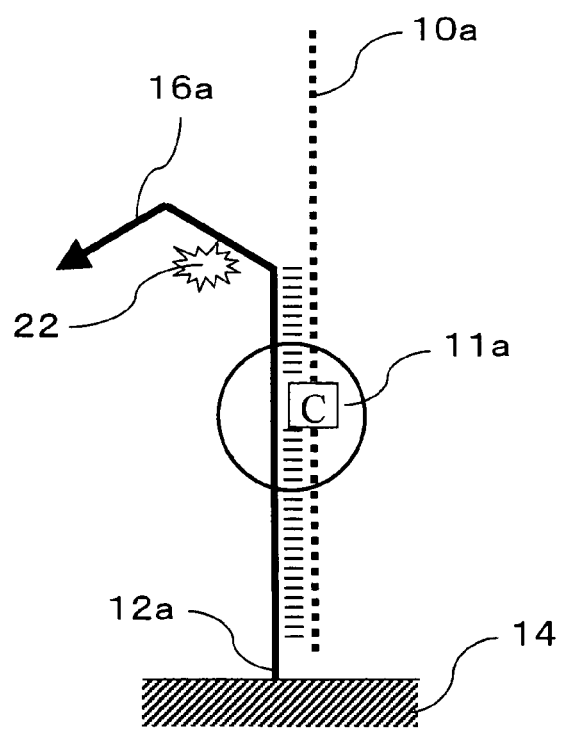
FIG. 4 is a schematic diagram showing in principle the step 112 in the first embodiment of order of steps of the signal amplification method of the present invention.
Figure 5:
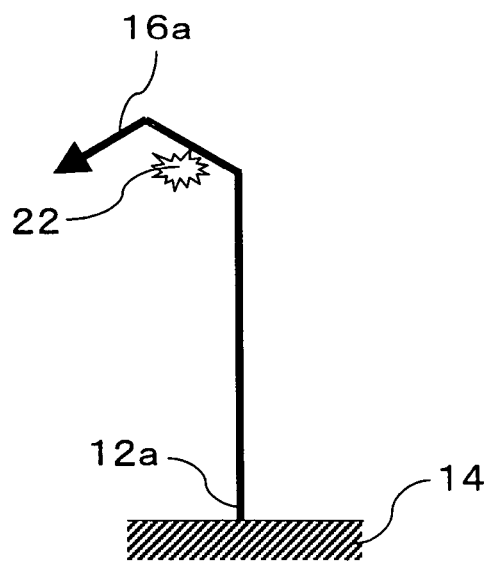
FIG. 5 is a schematic diagram showing in principle the step 114 in the first embodiment of order of steps of the signal amplification method of the present invention.

The mutation site 11a of the target DNA 10a is complementary to the end 13a of the capture probe 12a. Referring to FIG. 4, therefore, the capture probe 12a and the HCP-1 16a are joined by a ligation reaction (step 112). Referring to FIG. 5, after the ligation reaction, the target DNA 10a is removed (step 114). FIG. 5 shows that the capture probe 12a separated from the target DNA 10a and joined to the HCP-1 16a, is bound to the support 14.

Figure 6:
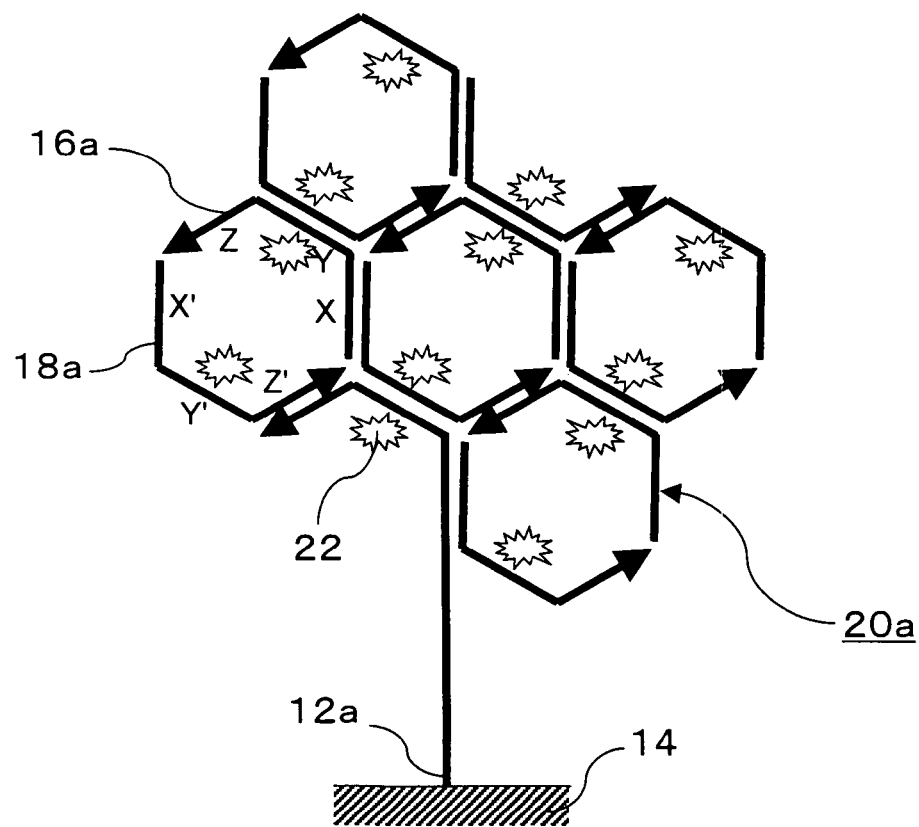
FIG. 6 is a schematic diagram showing in principle the step 116 in the first embodiment of order of steps of the signal amplification method of the present invention.

Referring to FIG. 6, a pair of the HCPs 16a and 18a is added to form a self-assembly substance 20a by a self-assembly reaction so that signal amplification can be achieved (step 116).

Figure 7:
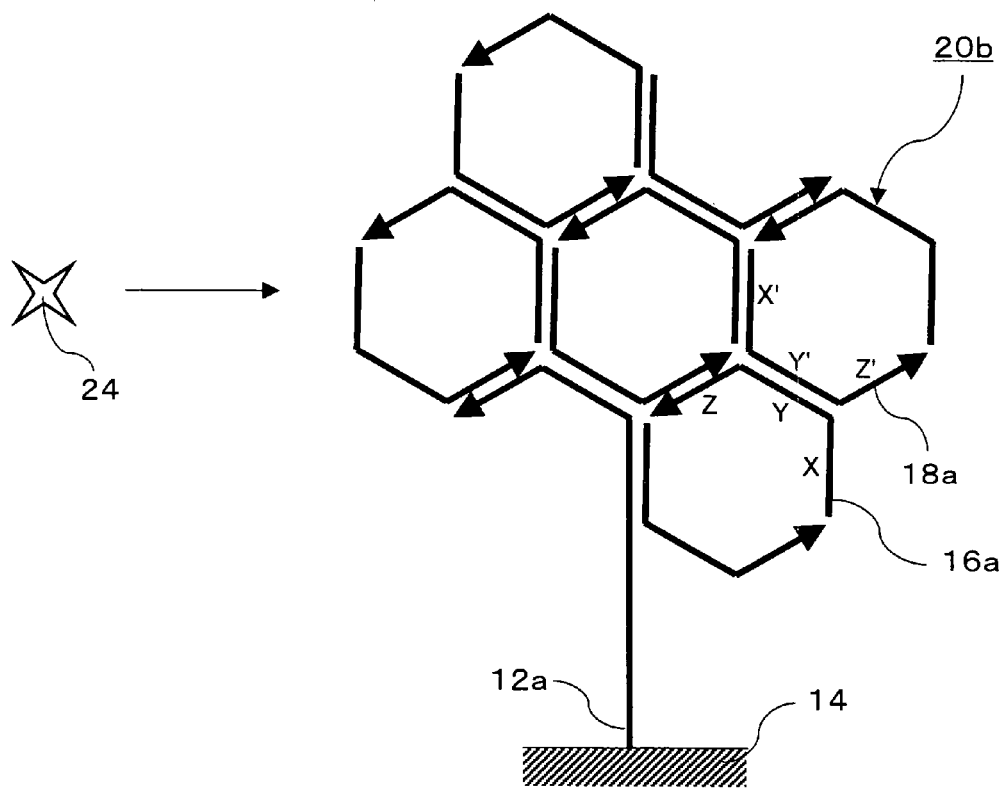
FIG. 7 is a schematic diagram showing in principle the step 124 in the second embodiment of order of steps of the signal amplification method of the present invention.
Figure 8:
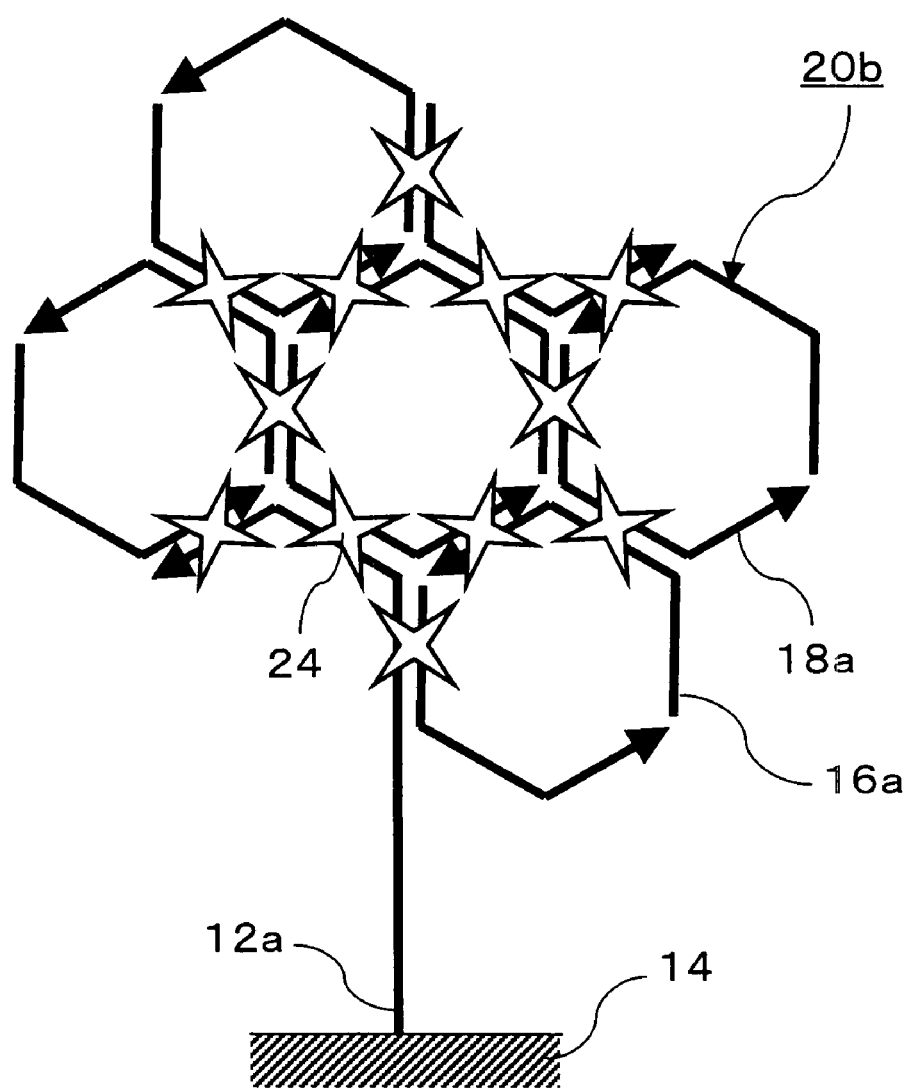
FIG. 8 is a schematic diagram showing in principle the step 126 in the second embodiment of order of steps of the signal amplification method of the present invention.

FIGS. 7 and 8 are schematic diagrams showing in principle the second embodiment of order of steps of the signal amplification method according to the present invention. The second embodiment shows an example of a signal amplification method according to the PALSAR method using a pair of the HCPs 16a and 18a, which has a region complementary to the target DNA 10a and is not labeled with the fluorescent substance 22.

Similarly to the first embodiment, after the steps 100 and 102 are performed, the HCP-1 16a is bound to the target DNA 10a with being adjacent to the capture probe 12a. The HCP-1 16a has a region complementary to the target DNA 10a and is one of the HCPs, wherein the HCPs can self-assemble by themselves to form an assembly.

After the capture probe 12a and the HCP-1 16a are joined to each other by a ligation reaction, the target DNA 10a is removed (step 120). A pair of the HCPs 16a and 18a is added to form a self-assembly substance 20b by a self-assembly reaction (step 122). Thereafter, referring to FIG. 7, an intercalator 24 is inserted into the formed self-assembly substance 20b (step 124) so that signal amplification can be achieved as shown in FIG. 8 (step 126). Incidentally, the steps 122 and 124 may be performed at the same time.

Figure 9:
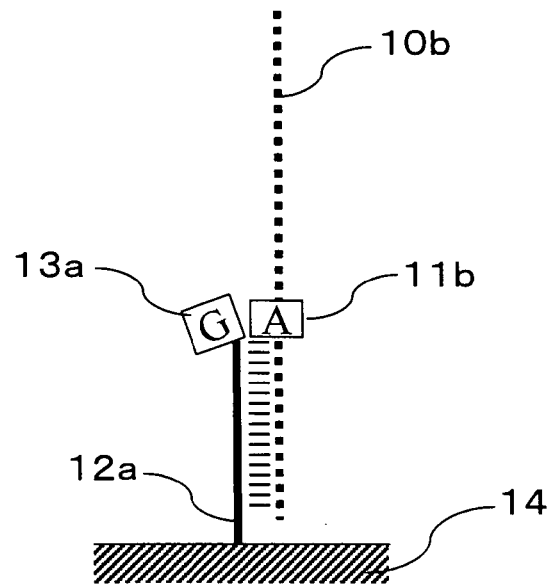
FIG. 9 is a schematic diagram showing in principle the step 200 in a reference embodiment in which the mutation site of the target DNA is not complementary to the end of the capture probe.
Figure 10:
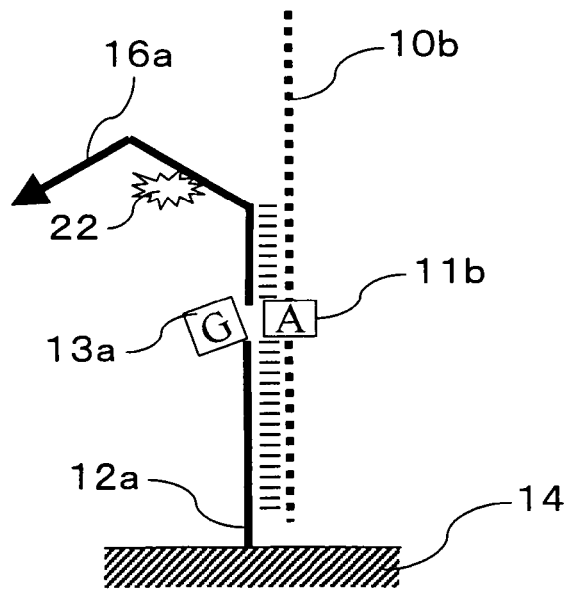
FIG. 10 is a schematic diagram showing in principle the step 202 in the reference embodiment in which the mutation site of the target DNA is not complementary to the end of the capture probe.
Figure 11:
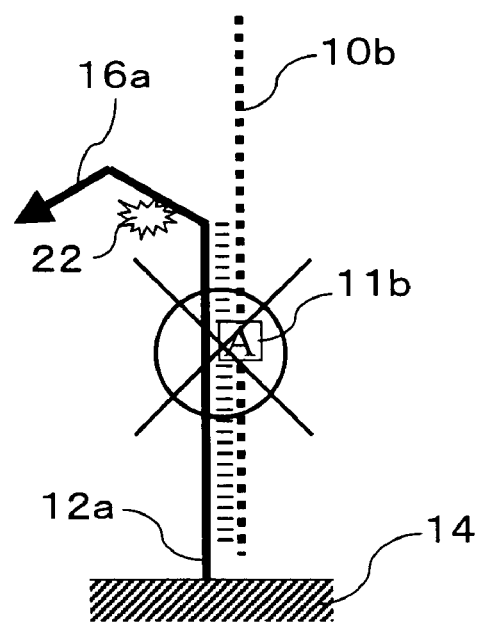
FIG. 11 is a schematic diagram showing in principle the step 204 in the reference embodiment in which the mutation site of the target DNA is not complementary to the end of the capture probe.
Figure 12:
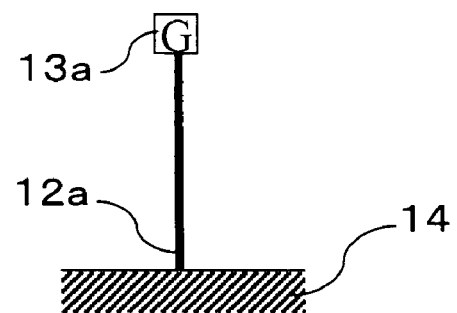
FIG. 12 is a schematic diagram showing in principle the step 206 in the reference embodiment in which the mutation site of the target DNA is not complementary to the end of the capture probe.

FIGS. 9 to 12 are schematic diagrams showing in principle a reference embodiment in which the mutation site of the target DNA 10b is not complementary to the end 13a of the capture probe 12a. Referring to FIG. 9, the target DNA 10b is captured (step 200). Thereafter, referring to FIG. 10, the HCP-1 16a is bound to the target DNA 10b with being adjacent to the capture probe 12a (step 202). The HCP-1 16a has a region complementary to the target DNA 10b and is one of the HCPs, wherein the HCPs are labeled with the fluorescent substance 22 and can self-assemble by themselves to form an assembly. Referring to FIG. 11, since the mutation site 11b of the target DNA 10b is not complementary to the end 13a of the capture probe 12a, no ligation reaction occurs (step 204). Referring to FIG. 12, when the target DNA 10b is separated (step 206), only the capture probe 12a is bound to the support 14. Thereafter, a pair of the HCPs 16a and 18a is added to form a self-assembly substance 20a, which is not bound to the capture probe 12a and thus removed by washing or the like so that signal amplification cannot be achieved.

Figure 13:
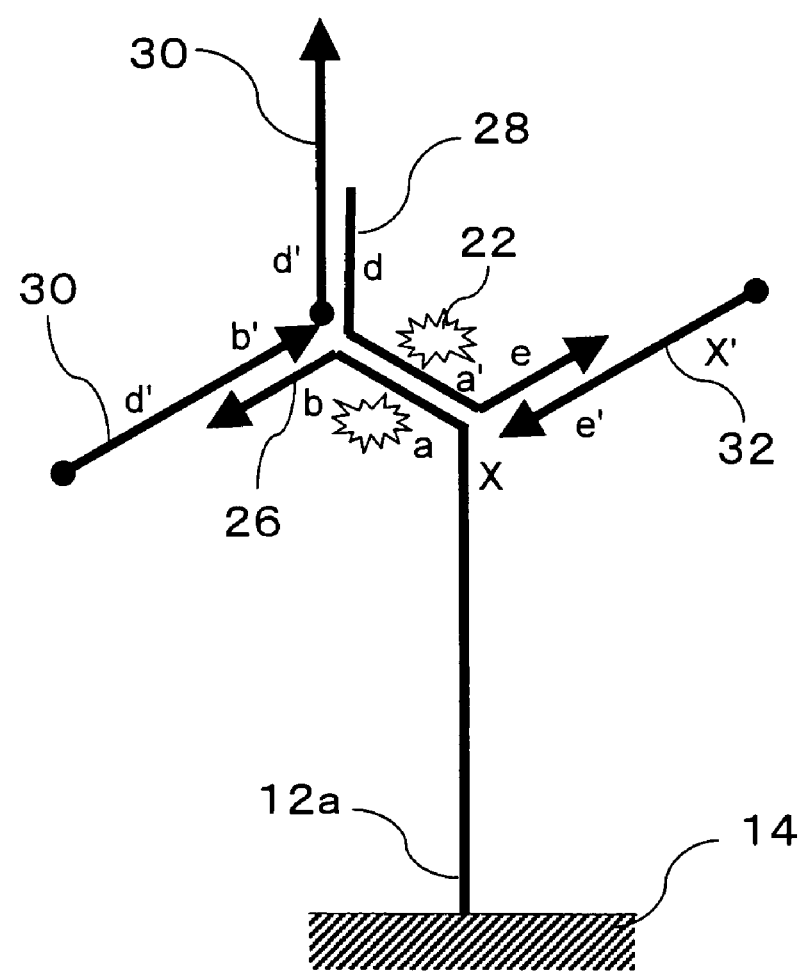
FIG. 13 is a schematic diagram showing in principle the step 136 in the third embodiment of order of steps of the signal amplification method of the present invention.
Figure 14:
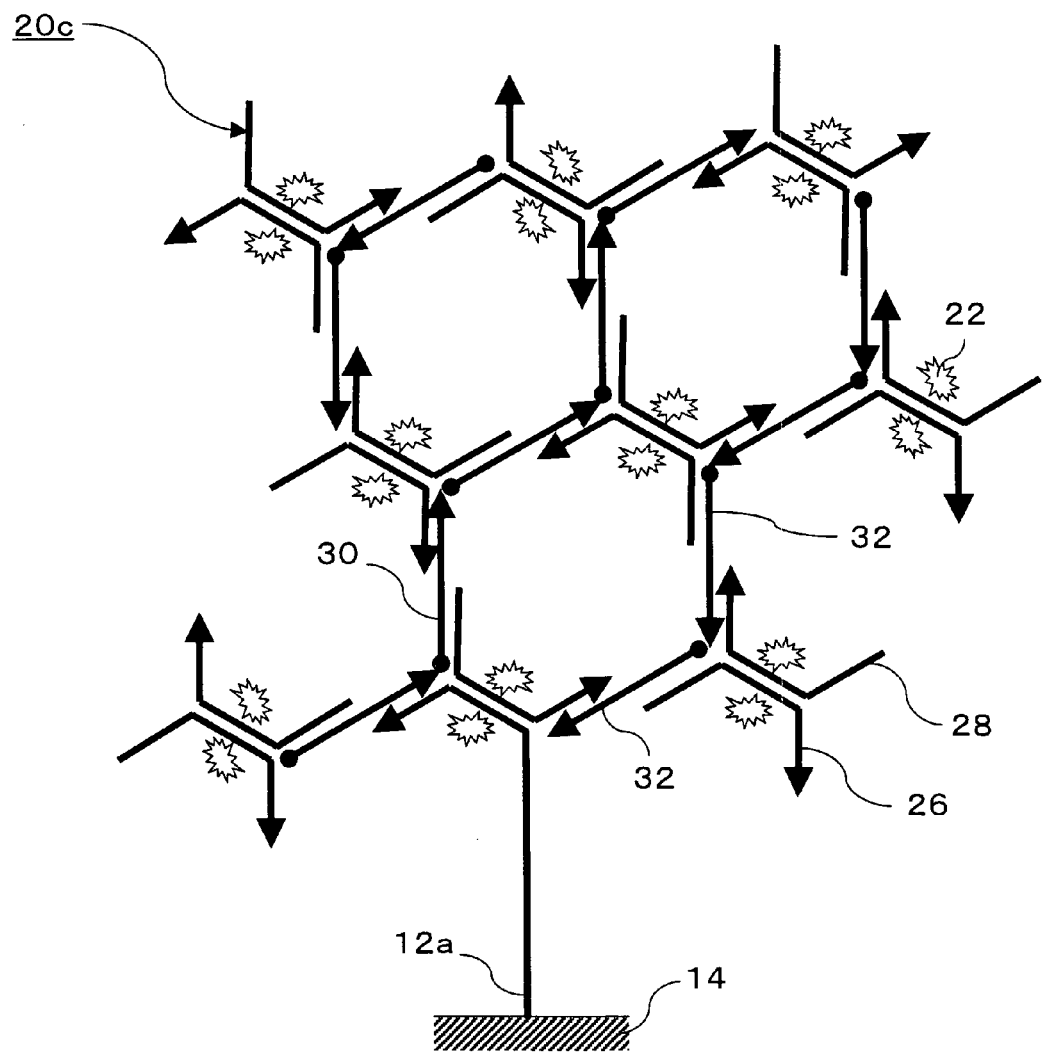
FIG. 14 is a schematic diagram showing in principle the step 138 in the third embodiment of order of steps of the signal amplification method of the present invention.

FIGS. 13 and 14 are schematic diagrams showing in principle the third embodiment of order of steps of the signal amplification method according to the present invention. In the third embodiment, the mutation site 11a of the target DNA 10a is complementary to an end 13a of the capture probe 12a. The third embodiment is a signal amplification method according to the PALSAR method using: a pair of dimer-forming probes (first and second dimer-forming probes: 5'-X-a-b-3' and 5'-d-a'-e-3' (26 and 28)) forming a dimer by themselves; and a pair of crosslinking probes (first and second crosslinking probes: 5'-d'-b'-3' and 5'-X'-e'-3' (30 and 32)) capable of crosslinking the dimer to be formed from the dimer-forming probes. The pair of dimer-forming probes 26 and 28 is in advance labeled with a fluorescent substance 22, and this embodiment uses the dimer formed from the pair of dimer-forming probes 26 and 28. Incidentally, the first dimer-forming probe 26 is constructed such that it has a region complementary to the target DNA 10a and hybridizes to the target DNA 10a with being adjacent to the capture probe 12a.

Similarly to the first example, after steps 100 and 102 are performed, the dimer having a region complementary to the target DNA 10a formed from the pair of the first and second dimer-forming probes 26 and 28 labeled with the fluorescent substance 22 is bound to the target DNA 10a with being adjacent to the capture probe 12a (step 130). Next, the capture probe 12a and the first dimer-forming probe 26 are joined by a ligation reaction (step 132). After the target DNA 10a is separated (step 134), referring to FIG. 13, the dimer formed from the first and second dimer-forming probes 26 and 28 and the first and second crosslinking probes 30 and 32 are then added. The probes 26, 28, 30, and 32 are hybridized (step 136). As a result, referring to FIG. 14, a self-assembly substance 20c is formed by a self-assembly reaction of the dimer-forming probes 26 and 28 and the crosslinking probes 30 and 32 so that signal amplification can be achieved (step 138).

Figure 15:
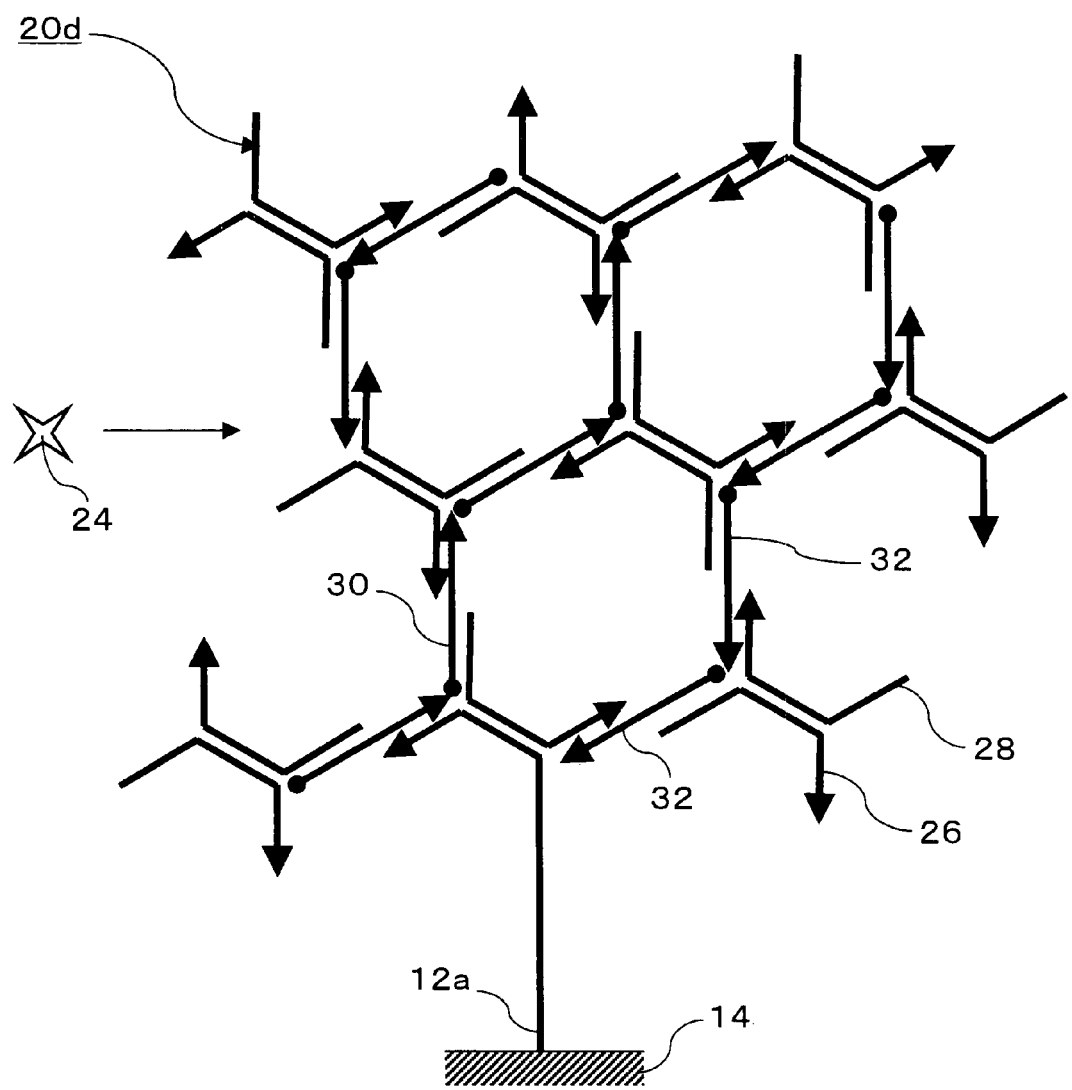
FIG. 15 is a schematic diagram showing in principle the step 146 in the fourth embodiment of order of steps of the signal amplification method of the present invention.
Figure 16:
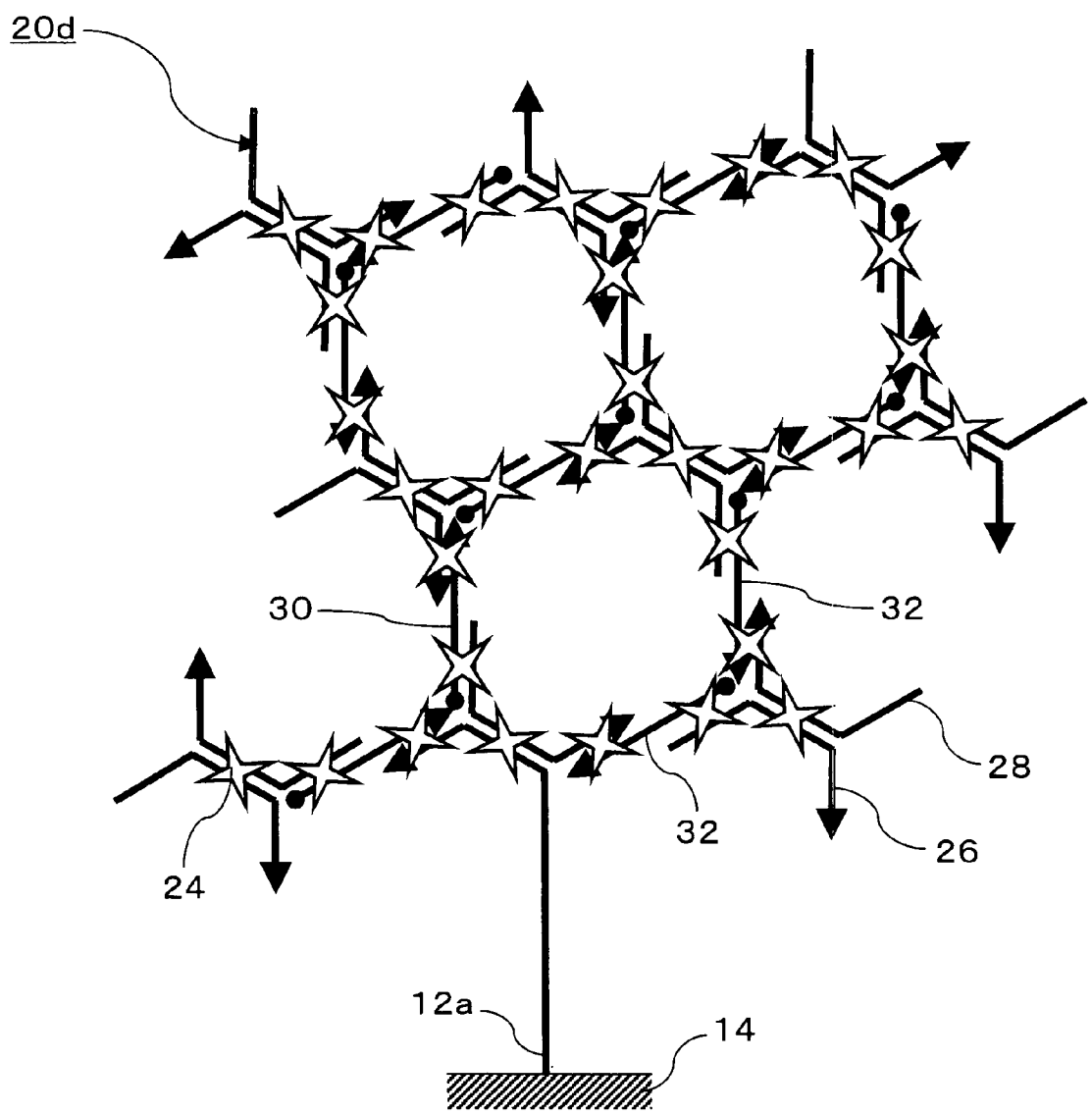
FIG. 16 is a schematic diagram showing in principle the step 148 in the fourth embodiment of order of steps of the signal amplification method of the present invention.

FIGS. 15 and 16 are schematic diagrams showing in principle the fourth embodiment of order of steps of the signal amplification method according to the present invention. The fourth embodiment is directed to a signal amplification method according to the PALSAR method using: a pair of dimer-forming probes (first and second dimer-forming probes 26 and 28) capable of forming a dimer by themselves; and a pair of crosslinking probes 30 and 32 capable of crosslinking the dimer formed from the dimer-forming probes. In this embodiment, the dimer formed from the pair of the dimer-forming probes is used, and the dimer-forming probes 26 and 28 and the crosslinking probes 30 and 32 are not labeled.

Similarly to the first embodiment, after the steps 100 and 102 are performed, there is bound the dimer formed from the pair of the first and second dimer-forming probes 26 and 28 having a region complementary to the target DNA 10a, to the target DNA 10a with being adjacent to the capture probe 12a (step 140).

After the capture probe 12a and the first dimer-forming probe 26 are joined by a ligation reaction, the target DNA 10a is removed (step 142). The dimer formed from the pair of the dimer-forming probes 26 and 28 and the pair of the crosslinking probes 30 and 32 are added to form a self-assembly substance 20d by a self-assembly reaction (step 144). Thereafter, referring to FIG. 15, an intercalator 24 is inserted into the formed self-assembly substance 20d (step 146) so that signal amplification can be achieved as shown in FIG. 16 (step 148). The steps 144 and 146 may be performed at the same time.

In the above embodiment, there is shown a case where one of the oligonucleotide probes for forming the self-assembly substance is the same as the first probe, but it is not necessarily the same as the first probe. For the purpose, there are usable probes which are designed such that the first probe and at least one of the oligonucleotide probes are capable of binding to each other.

In the above embodiment, there is used the capture probe which is in advance bound to the support. However, the capture probe may be bound to the support at any stage without limitation before the removal of the target DNA. For example, there is exemplified the stage after the target DNA is bound to the capture probe, after the capture probe, the target DNA and the first probe are all bound, or after the ligation reaction is carried out.

FIGS. 17 to 20 are schematic diagrams showing in principle the fifth embodiment of order of steps of the signal amplification method according to the present invention. The fifth embodiment is directed to a method for simultaneously detecting different mutated genes, which uses a pair of the HCPs 16e and 18e and first probes 34e, 34f and 34g having sequences complementary to target DNAs 10e, 10f and 10g at a terminal region thereof, respectively, and each of the probes includes two HCP regions. The number of the first probes should be as many as that of the target genes. In this embodiment, three kinds of genes 10e, 10f and 10g are provided, and thus there are used three kinds of first probes 34e, 34f and 34g that are different in their terminal regions. Since the two regions of each of the first probes other than the terminal region of each thereof have a common HCP sequence, signal amplification can be achieved using a single pair of the HCPs regardless of the kinds of the first probes.

Figure 17:
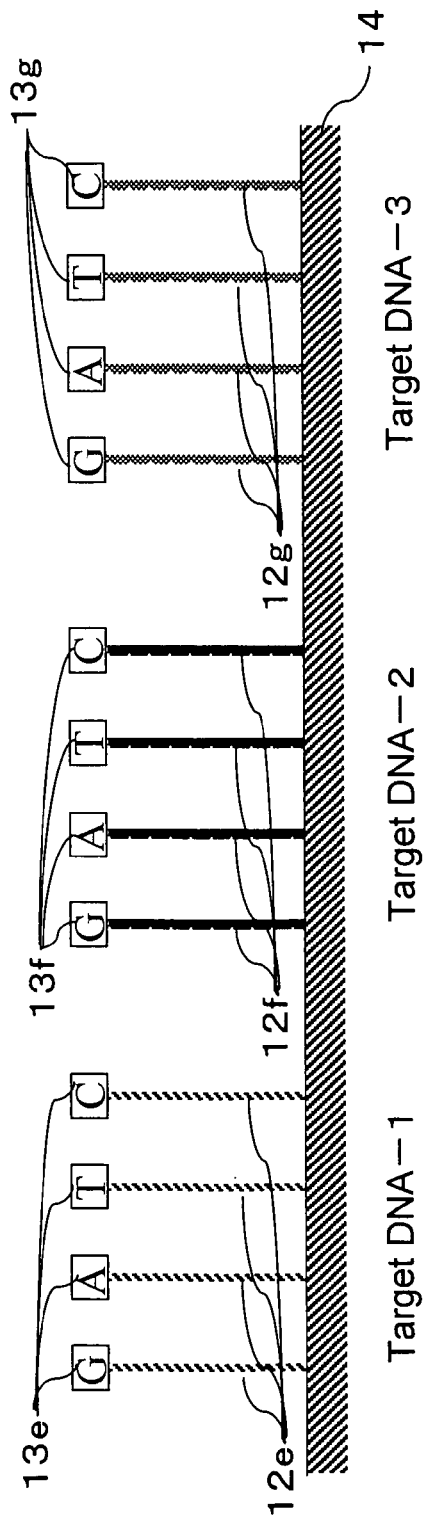
FIG. 17 is a schematic diagram showing in principle the step 150 in the fifth embodiment of order of steps of the signal amplification method of the present invention.
Figure 18:
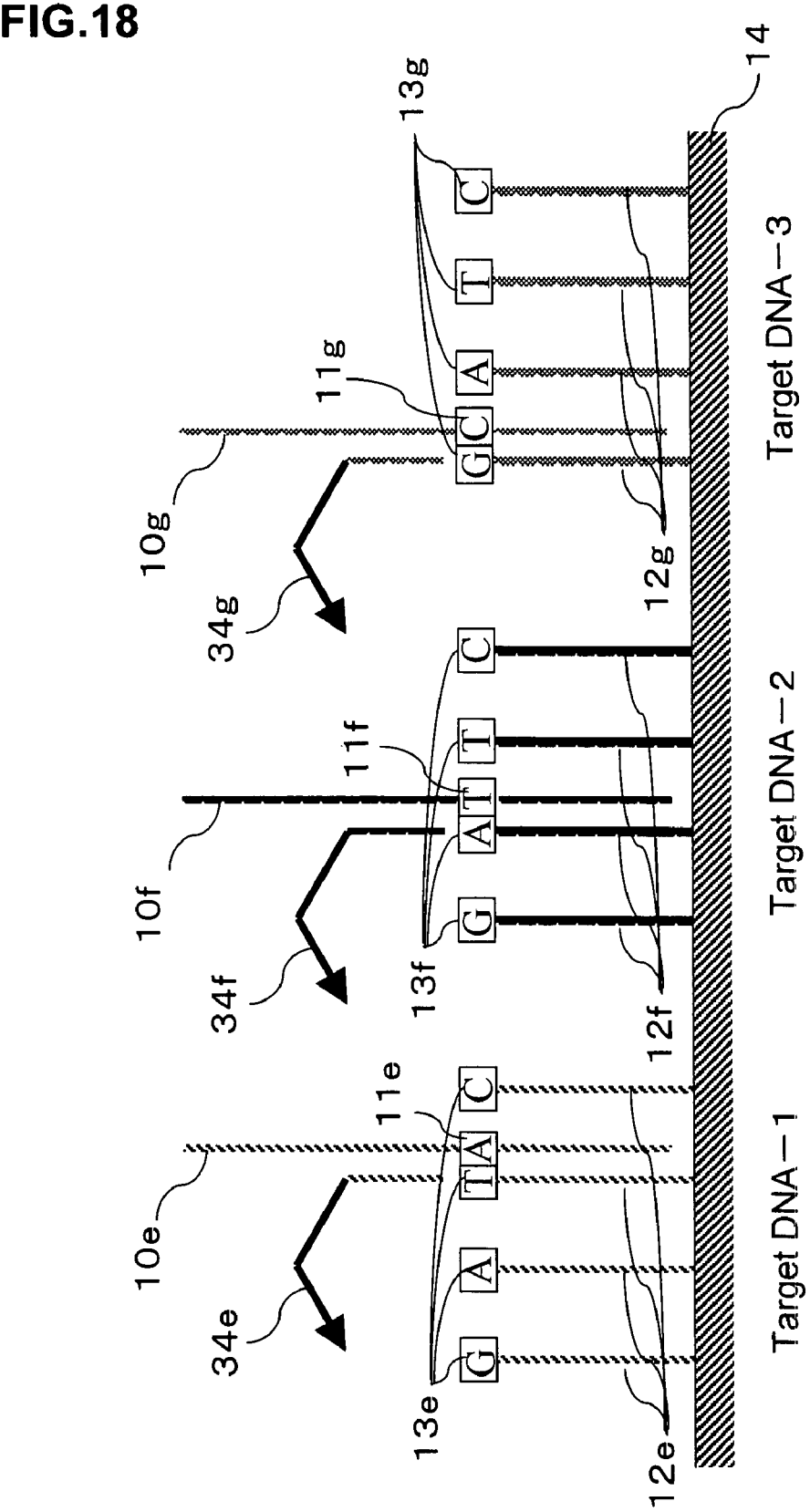
FIG. 18 is a schematic diagram showing in principle the step 152 in the fifth embodiment of order of steps of the signal amplification method of the present invention.
Figure 19:
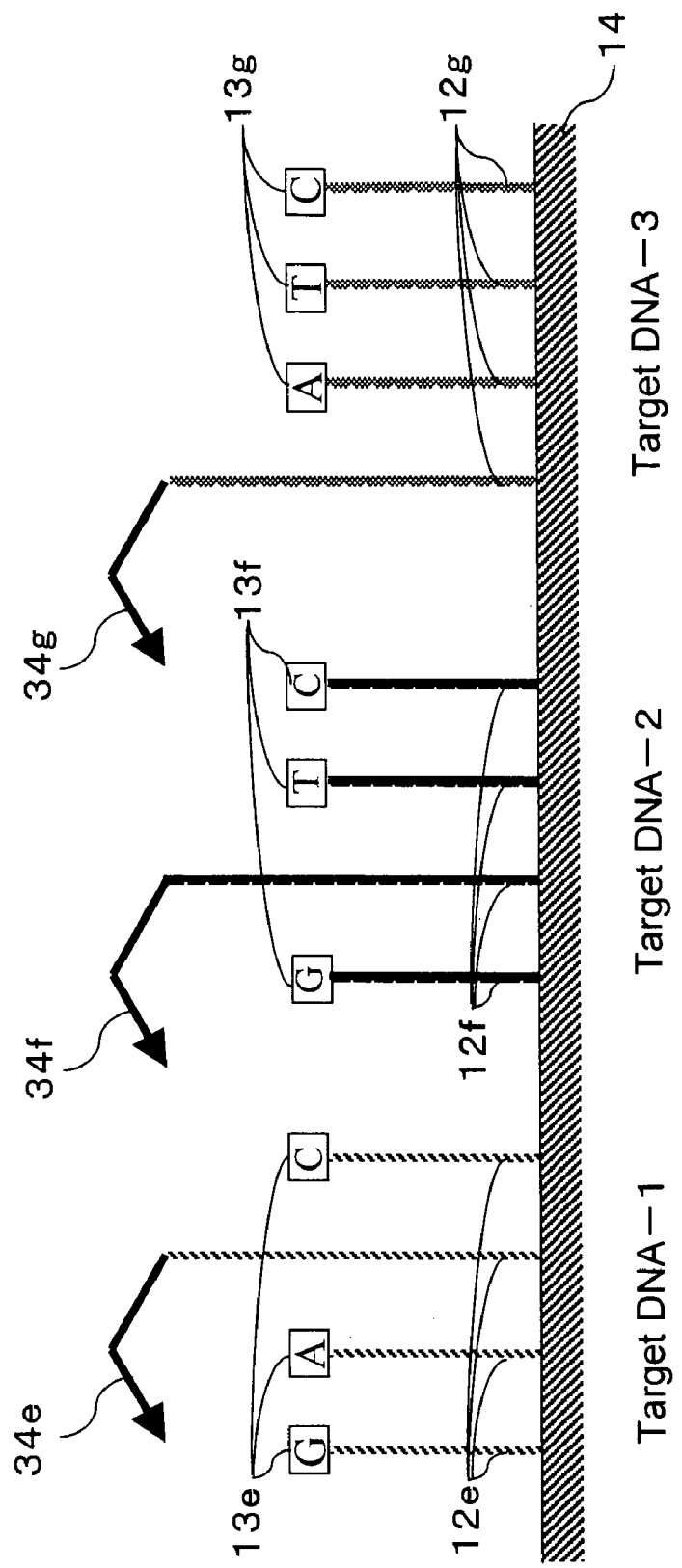
FIG. 19 is a schematic diagram showing in principle the step 154 in the fifth embodiment of order of steps of the signal amplification method of the present invention.

Referring to FIG. 17, there are independently bound onto a support 14 four kinds of capture probes 12e constructed such that each thereof has a region complementary to a target DNA-1 (10e), each end 13e thereof is located at a gene mutation site 11e of the target DNA-1 and the four kinds of capture probes 12e are different from each other in base of the end thereof; four kinds of capture probes 12f constructed such that each thereof has a region complementary to a target DNA-2 (10f), each end 13f thereof is located at a gene mutation site 11f of the target DNA-2 and the four kinds of capture probes 12f are different from each other in base of the end thereof; and four kinds of capture probes 12g constructed such that each thereof has a region complementary to a target DNA-3 (10g), each end 13g thereof is located at a gene mutation site 11g of the target DNA-3 and the four kinds of capture probes 12g are different from each other in base of the end thereof (step 150). Incidentally, in FIGS. 17 to 20, the capture probes only different in the end and their ends are represented by the same reference character, respectively. Next, referring to FIG. 18, the target DNAs 10e, 10f and 10g and the first probes 34e, 34f and 34g are bound in response to the capture probes 12e, 12*f* and 12*g* (step 152). Even if the mutation site is not complementary, the portion other than the end is similarly bound, but this drawing shows only the case that the end is complementary. Then, referring to FIG. 19, after a ligation reaction, the target DNAs 10*e*, 10*f* and 10*g* and the unreacted probes are removed (step 154).

Figure 20:
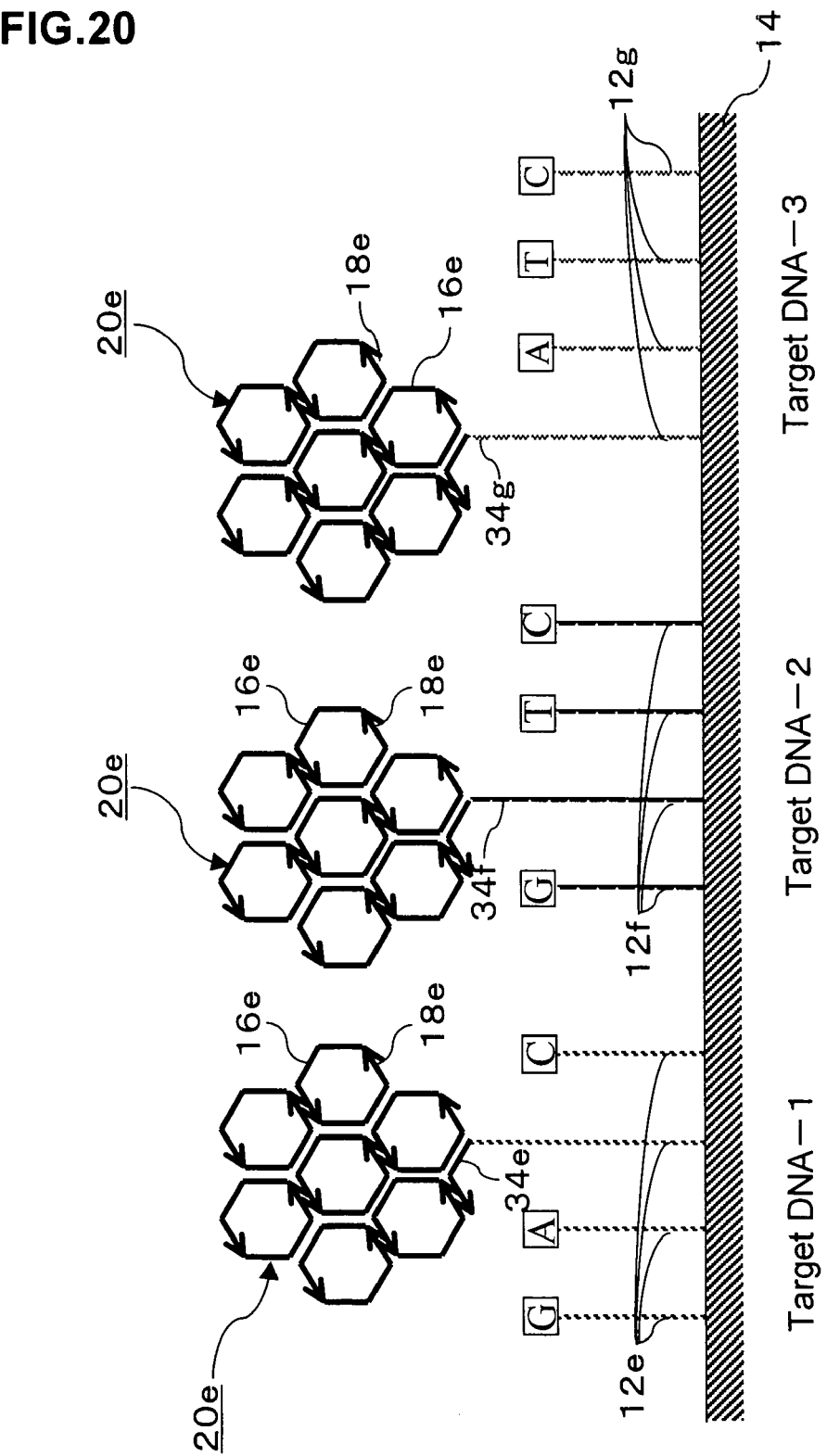
FIG. 20 is a schematic diagram showing in principle the step 156 in the fifth embodiment of order of steps of the signal amplification method of the present invention.

Referring to FIG. 20, a pair of the HCPs 16*e* and 18*e* is added to form a self-assembly substance 20*e* so that signal amplification can be achieved (step 156). In the fifth embodiment, the four bases are all examined with respect to the gene mutation sites. However, any base or bases may be selected as the end of the capture probe as needed, and any special limitation is not imposed thereon.

FIGS. 21 to 26 are schematic diagrams showing in principle the sixth embodiment of order of steps of the signal amplification method according to the present invention. The sixth embodiment is characterized in that the ligation reaction is performed at two sites so that a first probe 34*h* joined the HCP-1 (16*h*) to a capture probe 12*h*. The HCP-1 (16*h*), the first probe 34*h* and the capture probe 12*h* are designed with being adjacent to each other. For simultaneous detection of different mutated genes, similarly to the fifth embodiment, common oligonucleotides may be used as a second probe and a pair of the HCPs regardless of the gene types, except that the end region of the first probe is complementary to each target DNA.

Figure 21:
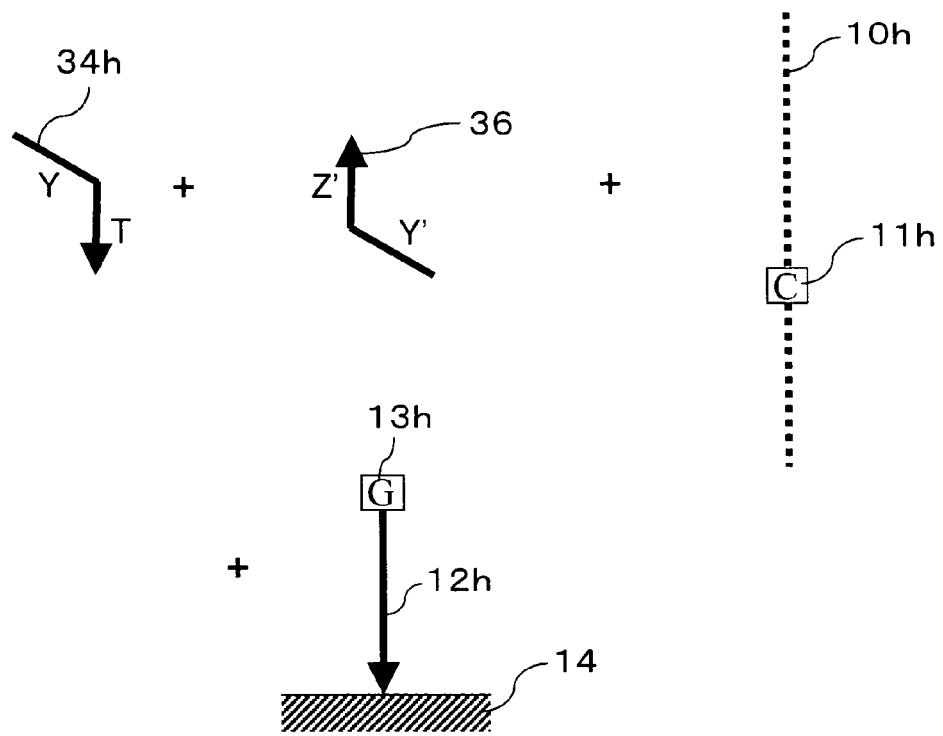
FIG. 21 is a schematic diagram showing in principle the step 160 in the sixth embodiment of order of steps of the signal amplification method of the present invention.
Figure 22:
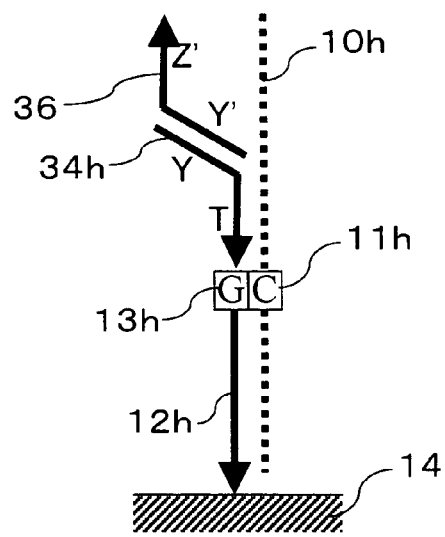
FIG. 22 is a schematic diagram showing in principle the step 162 in the sixth embodiment of order of steps of the signal amplification method of the present invention.
Figure 23:
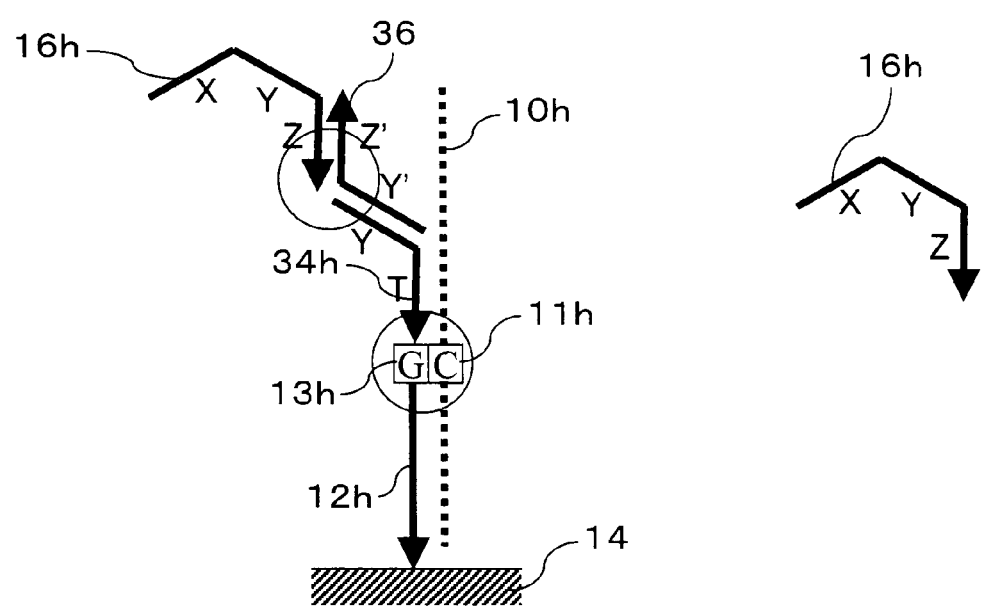
FIG. 23 is a schematic diagram showing in principle the step 163 in the fifth embodiment of order of steps of the signal amplification method of the present invention.
Figure 24:
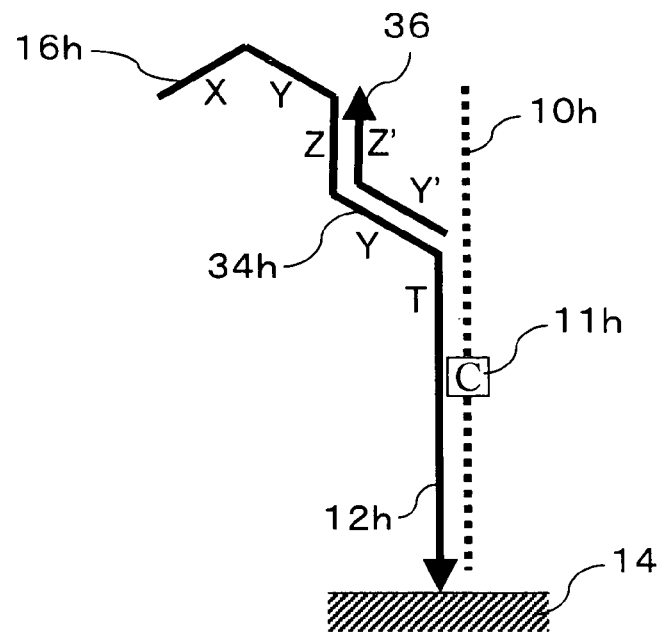
FIG. 24 is a schematic diagram showing in principle the step 164 in the sixth embodiment of order of steps of the signal amplification method of the present invention.
Figure 25:
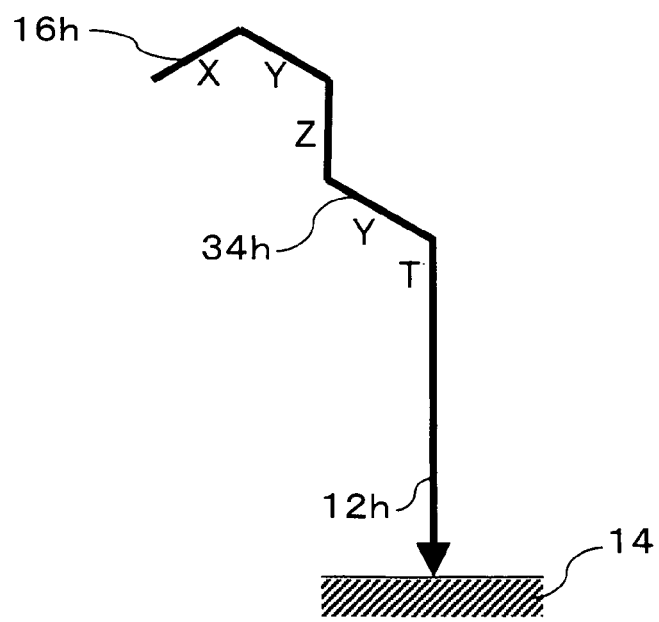
FIG. 25 is a schematic diagram showing in principle the step 165 in the sixth embodiment of order of steps of the signal amplification method of the present invention.
Figure 26:
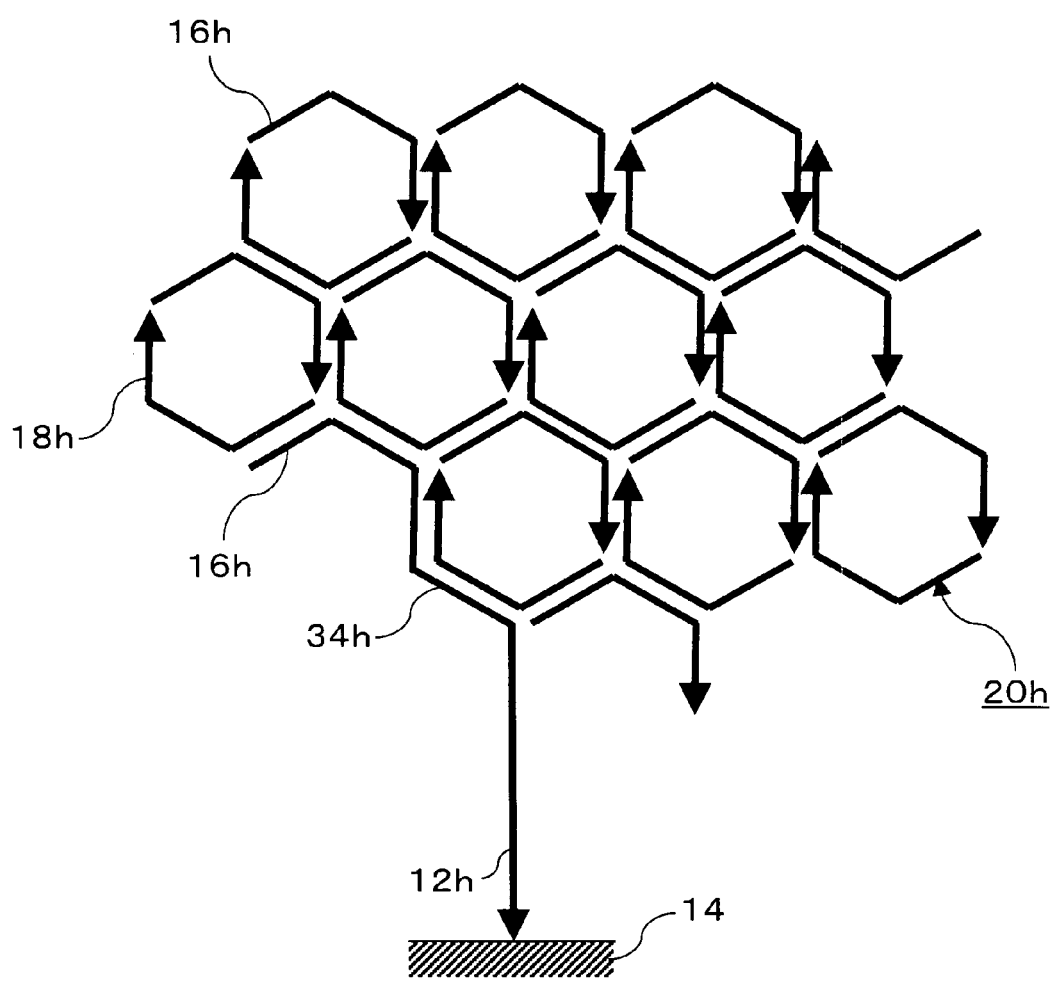
FIG. 26 is a schematic diagram showing in principle the step 166 in the sixth embodiment of order of steps of the signal amplification method of the present invention.

FIG. 21 shows the first probe 34*h*, the second probe 36, the target DNA 10*h*, and the capture probe 12*h* fixed on the support 14 (step 160). The first probe 34*h* has a sequence complementary to the target DNA 10*h*, and a sequence part identical to that of the HCP-1 (16*h*). The second probe 36 has two sequence parts identical to those of the HCP-2 (18*h*). Referring to FIG. 22, the first probe 34*h* is hybridized to both the second probe 36 and the target DNA 10*h* (step 162). Referring to FIG. 23, the HCP-1 (16*h*) is added for hybridization. The HCP-1 (16*h*) is hybridized to the second probe 36 so that the HCP-1 (16*h*) adjoins the first probe 34*h*. As a result, there are both ends of the first probe 34*h* adjoining the capture probe 12*h* and the HCP-1 16*h*, respectively (step 163). Incidentally, steps 162 and 163 may be performed at the same time. Referring to FIGS. 24 and 25, if the end portion 13*h* of the capture probe 12*h* is complementary to the mutation site 11*h* of the target DNA 10*h*, after ligation reaction (step 164), removal of the target DNA 10*h*, the second probe 36 and the unreacted probes leads to a state where the capture probe 12*h*, the first probe 34*h* and the HCP-1 (16*h*) are connected in the form of a strand (step 165). Referring to FIG. 26, a pair of the HCPs 16*h* and 18*h* is added to form a self-assembly substance 20*h* (step 166) so that signal amplification can be achieved.

In the signal amplification method of the present invention, a labeling substance for detection may previously be added to a pair of oligonucleotide probes for detection of the target DNA. Examples of such a labeling substance include a radioisotope such as $^{125}$I and $^{32}$P, luminescent substances such as digoxigenin and acridinium esters, fluorescent substances such as Cy3 and Cy5, and donor and acceptor fluorescent dyes for using fluorescent resonance energy transfer (FRET) such as biotin for using a fluorescent substance such as 4-methylunbelliferyl phosphate.

Alternatively, by adding a dye having the property of binding to nucleic acids, the target gene can be detected. As shown in FIGS. 8 and 16, a fluorescent material having the property of binding to nucleic acids, such as an intercalator, is preferably used to detect the target gene. Any fluorescent material having the property of binding to nucleic acids may be used without limitation. Examples of such a fluorescent material include SYBR Green I stain, SYBR Green II stain, SYBR Green Gold stain, Vista Green stain, Gelstar stain, Radlant Red stain, PicoGreen, RiboGreen, O11Green, Hoechst 33258 (Bis-Benzimide), Propidium Iodide, YO-PRO-1 Iodide, YO-PRO-3 Iodide (the above materials are all manufactured by Molecular Probes Inc.), ethidium bromide, Distamycin A, TOTO, Psoralen, acridinium orange (Acridine Orange), AOAO (homodimer), and the like.

While a nucleic acid constituting the pair of the oligonucleotides is usually DNA or RNA, a nucleic acid analogue may constitute them. Examples of such a nucleic acid analogue include peptide nucleic acid (PNA, for example, see the brochure of International Patent Publication No. WO 92/20702) and locked nucleic acid (LNA, for example, see Koshkin A A et al., Tetrahedron 1998, 54, 3607-3630, Koshkin A A et al., J. Am. Chem. Soc., 1998, 120, 13252-13253 and Wahlestedt C et al., PNAS, 2000, 97, 5633-5638). The pair of the oligonucleotide probes is generally composed of nucleic acids of the same kind, but may be composed of a pair of a DNA probe and an RNA probe. That is, the type of the nucleic acid of the probe may be selected from DNA, RNA or nucleic acid analogues (such as PNA and LNA). Also, it is not necessary that a single probe is composed of a single type of nucleic acid, for example, DNA only, and, if necessary, for example, an oligonucleotide probe composed of DNA and RNA (a chimera probe) may be used in an aspect of the present invention.

In the present invention, any sample potentially containing a target nucleic acid may be used as a sample for the measurement of a target gene. The target gene may be any properly prepared or isolated from samples and it is not specifically limited. Examples of such samples include organism-derived samples such as blood, blood serum, urine, feces, cerebrospinal fluid, tissue fluid, and cell cultures, and any samples potentially containing or potentially infected with viruses, bacteria, fungi, or the like. There may be also used any nucleic acid obtained by amplifying a target gene in samples with any known method.

In the drawings, the distal arrow mark represents the 3' end, and the proximal black dot represents the 5' end.

EXAMPLES

Although the present invention is more specifically described by means of the examples below, it will be understood that the examples presented are by way of illustration only and should not be construed as any limitation on the present invention.

Example 1

1. Purpose

Using the PALSAR method, detection of mutated genes was conducted based on a difference in the base of mutation site of the end.

2. Materials

The following are the base sequences of the oligonucleotide probes used in Example 1.

(1) Capture Probes

```
CP-1-A:
5'(amino group)-GG GGAAGAGCAGAGATATACGTA-3'

CP-1-T:
5'(amino group)-GG GGAAGAGCAGAGATATACGTT-3'
```

-continued

```
CP-1-G:
5'(amino group)-GG GGAAGAGCAGAGATATACGTG-3'

CP-1-C:
5'(amino group)-GG GGAAGAGCAGAGATATACGTC-3'
```

(2) Target Gene-1 (Materials synthesized based on the base sequence of a Hemochromatosis gene, wherein the mutation site (corresponding to the 845th amino acid residue) is underlined)

```
Target Gene-1-T
5'-GGC CTGGGTGCTCCACCTGG TACGTATATCTCTGCTCTTCC-3'

Target Gene-1-A:
5'-GGC CTGGGTGCTCCACCTGG AACGTATATCTCTGCTCTTCC-3'

Target Gene-1-C:
5'-GGC CTGGGTGCTCCACCTGG CACGTATATCTCTGCTCTTCC-3'

Target Gene-1-G:
5'-GGC CTGGGTGCTCCACCTGG GACGTATATCTCTGCTCTTCC-3'
```

(3) First Probe

```
First Probe-1a:
5'(phosphorylated)-CCAGGTGGAGCACCCAG CATATGTA
GCAGAGCGTAAGTCATGTCCACC-3'  (Alexa532 label)
```

(4) HCP

```
HCP-1-1:
5'(Cy3 label)-CCAGGTGGAGCACCCA GCATATGTAGCAGAGC
GTAAGTCATGTCCACC-3'

HCP-1-2:
5'(Cy3 label)-TGGGTGCTCCACCTGG GCTCTGCTACATATGC
GGTGGACATGACTTAC-3'
```

A hybridization solution was prepared (final concentration: 6×SSC, 0.1 mg/mL salmon sperm DNA, 5×Denhardt's solution, and 0.2% SDS).

A coated slide glass for microarray immobilized amino-modified oligo DNA (manufactured by Matsunami Glass Ind., Ltd.) was used as a substrate for fixing the capture probes. A DNA Microarrayer 32-pin model (manufactured by Greiner Bio-One Co., Ltd.) was used as a spotter.

3. Methods 3-1. Preparation of Slide Glass (a) Spotting of Capture Probes

Each capture probe (100 pmol/μL) and a spotting solution (manufactured by Matsunami Glass Ind., Ltd.) were mixed by the same amounts so that four types of probe solutions were prepared. The resulting probe solutions were spotted on the slide glass in the manner of N=4. When spotting another probe solution, the pins were washed with sterilized water and cold ethanol, and then air-dried. The spotted slide glass was placed in a wetting box and left overnight while shielded from light.

(b) Immobilization of Capture Probes

A vat of a blocking solution (manufactured by Matsunami Glass Ind., Ltd.), two vats of sterilized water and a vat of cold methanol were provided, each vat being a dyeing vat. The spotted slide glass was sequentially immersed in the blocking solution for 20 minutes, each vat of the sterilized water for 3 minutes and the cold methanol for 3 minutes so that the immobilization of the capture probe was performed. Thereafter, the slide glass was air-dried and finished.

3-2. Detection (a) Hybridization Reaction

Each target gene was added to each of the four hybridization solutions at a concentration of 30 pmol (30 μL), and the first probe was also added at a concentration of 30 pmol (30 mL). Each solution (25 μL) was subjected to thermal dissociation at 95° C. for 2 minutes and then reacted in a chamber on the slide glass immobilized the capture probes at 42° C. for 2 hours to hybridize each capture probe, each target gene and the first probe. After the reaction, the slide glass was washed twice with a 2×SSC and 0.1% SDS solution, once with a 1×SSC solution and once with a 0.2×SSC solution and then air-dried.

(b) Ligation Reaction and Alkali Denaturation

A thermostable ligase (Tth DNA ligase) was used as a ligase. The ligase (30 U) was added to 30 μL of a buffer attached to the ligase, and 25 μL of the resulting solution was reacted in the chamber under the conditions of 65° C. and 15 minutes.

After the ligation reaction, the slide glass was lightly washed with a 0.2×SSC solution and then subjected to alkali treatment with a 0.25 M NaOH solution for 10 minutes so that the unreacted probes and the excessive probes were removed. A 0.25 M HCl solution was used to neutralize the NaOH solution. After the denaturation, the slide glass was washed twice with a 2×SSC and 0.1% SDS solution, once with a 1×SSC solution and once with a 0.2×SSC solution and then air-dried.

(c) Self-Assembly Substance Forming Reaction

A pair of HCPs (HCP-1-1 and HCP-1-2) each labeled with Cy3 at the 5' end was added to the hybridization solution at a final concentration of 1 pmol/μL. The solution was subjected to thermal dissociation at 95° C. for 2 minutes and 25 μL thereof was reacted in the chamber on the slide glass, which had been washed and dried after the alkali denaturation, at 68° C. for 2 hours to form a self-assembly substance. After the reaction, the slide glass was washed twice with a 2×SSC and 0.1% SDS solution, once with a 1×SSC solution and once with a 0.2×SSC solution and then air-dried. The fluorescence of Cy3 on the slide glass was observed with a fluorescence microscope. The result is shown in FIG. 27.

Figure 27:
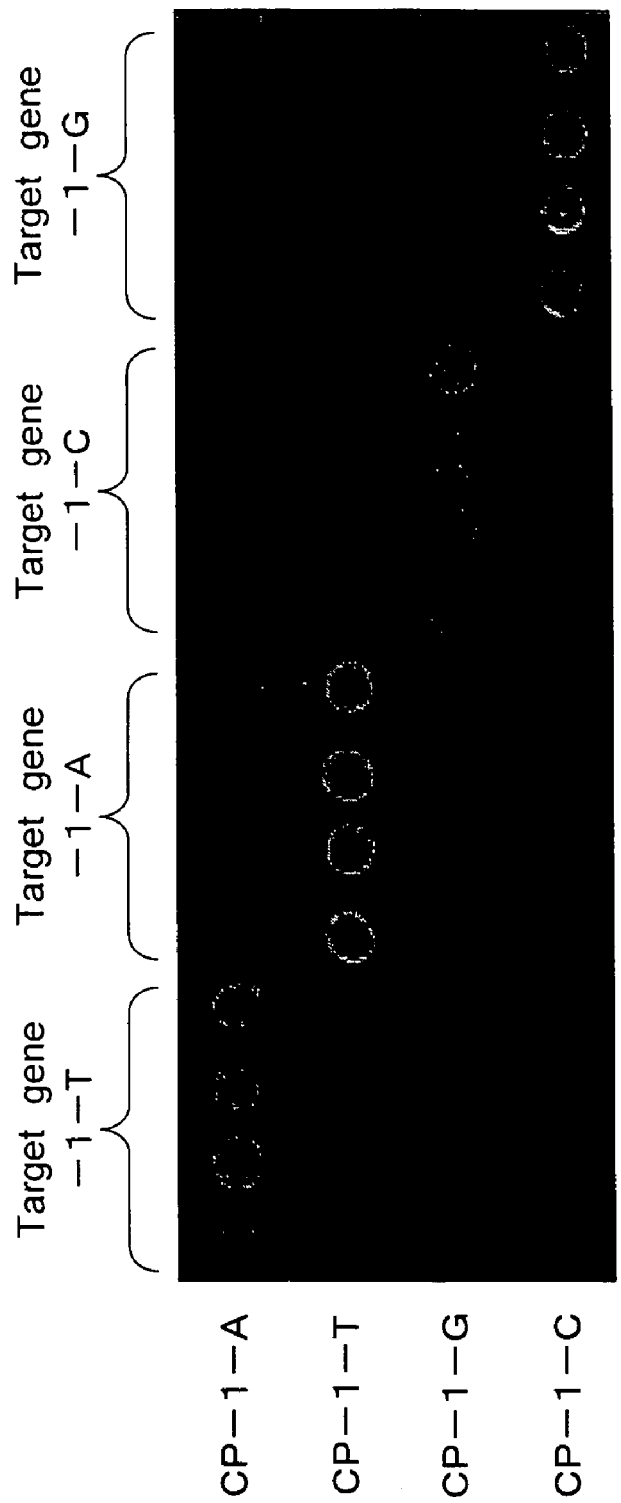
FIG. 27 is a photograph showing the result of Example 1.

FIG. 27 indicates that signal was amplified only when the mutation site of the target gene was complementary to the capture probe.

Example 2

1. Purpose

Multiplex detection was conducted with respect to 12 types of genes.

2. Materials

The following are the base sequences of the oligonucleotide probes used in Example 2.

(1) Capture Probes

```
CP-1-G:   the same as CP-1-G of Example 1

CP-1-A:   the same as CP-1-A of Example 1
```

-continued

```
CP-2-T:     5'(amino group)-GCGCGGACATGGAGGACGTGT-3'

CP-2-C:     5'(amino group)-GCGCGGACATGGAGGACGTGC-3'

CP-3-C:     5'(amino group)-ATGCCGATGACCTGCAGAAGC-3'

CP-3-T:     5'(amino group)-ATGCCGATGACCTGCAGAAGT-3'

CP-4-G:     5'(amino group)-CTTGAATTCCAAGAGCACACG-3'

CP-4-A:     5'(amino group)-CTTGAATTCCAAGAGCACACA-3'

CP-5-C:     5'(amino group)-GGAGAAGGTGTCTGCGGGAGC-3'

CP-5-T:     5'(amino group)-GGAGAAGGTGTCTGCGGGAGT-3'

CP-6-A:     5'(amino group)-TGCTGGCTGAAATGGCAATGA-3'

CP-6-G:     5'(amino group)-TGCTGGCTGAAATGGCAATGG-3'

CP-7-A:     5'(amino group)-TGTTCTGGGTACTACAGCAGA-3'

CP-7-G:     5'(amino group)-TGTTCTGGGTACTACAGCAGG-3'

CP-8-C:     5'(amino group)-TGGATGATTTGATGCTGTCCC-3'

CP-8-T:     5'(amino group)-TGGATGATTTGATGCTGTCCT-3'

CP-9-G:     5'(amino group)-AATGCCAGAGGCTGCTCCCG-3'

CP-9-C:     5'(amino group)-AATGCCAGAGGCTGCTCCCC-3'

CP-10-C:    5'(amino group)-AGCTGTTCGTGTTCTATGATC-3'

CP-10-G:    5'(amino group)-AGCTGTTCGTGTTCTATGATG-3'

CP-11-G:    5'(amino group)-ACTTGTGGTAGTTGGAGCTGG-3'

CP-11-T:    5'(amino group)-ACTTGTGGTAGTTGGAGCTGT-3'

CP-12-A:    5'(amino group)-TATTCTCGACACAGCAGGTCA-3'

CP-12-T:    5'(amino group)-TATTCTCGACACAGCAGGTCT-3'
```

(2) First Probes

```
First Probe-1b:
5'(phosphorylated)-CCAGGTGGAGCACCCAGGCC GAACTATGCC
GATAACCGTG GTATAGTACGCTTGCACGTG CCCGTACATGCGTTGTAA
TG-3'

First Probe-2:
5'(phosphorylated)-GCGGCCGCCTGGTGCAGTAC GAACTATGCC
GATAACCGTG GTATAGTACGCTTGCACGTG CCCGTACATGCGTTGTAA
TG-3'

First Probe-3:
5'(phosphorylated)-GCCTGGCAGTGTACCAGGCC GAACTATGCC
GATAACCGTG GTATAGTACGCTTGCACGTG CCCGTACATGCGTTGTAA
TG-3'

First Probe-4:
5'(phosphorylated)-GTCTTCAGTGAAGCTGCAGG GAACTATGCC
GATAACCGTG GTATAGTACGCTTGCACGTG CCCGTACATGCGTTGTAA
TG-3'

First Probe-5:
5'(phosphorylated)-CGATTTCATCATCACGCAGC GAACTATGCC
GATAACCGTG GTATAGTACGCTTGCACGTG CCCGTACATGCGTTGTAA
TG-3'

First Probe-6:
5'(phosphorylated)-AAGTTGAACTAGCTAGAATG GAACTATGCC
GATAACCGTG GTATAGTACGCTTGCACGTG CCCGTACATGCGTTGTAA
TG-3'

First Probe-7
5'(phosphorylated)-AGGGTATGCGGAAGCGAGCA GAACTATGCC
GATAACCGTG GTATAGTACGCTTGCACGTG CCCGTACATGCGTTGTAA
TG-3'

First Probe-8
5'(phosphorylated)-CGGACGATATTGAACAATGG GAACTATGCC
GATAACCGTG GTATAGTACGCTTGCACGTG CCCGTACATGCGTTGTAA
TG-3'

First Probe-9
5'(phosphorylated)-CGTGGCCCCTGCACCAGCAG GAACTATGCC
GATAACCGTG GTATAGTACGCTTGCACGTG CCCGTACATGCGTTGTAA
TG-3'

First Probe-10
5'(phosphorylated)-ATGAGAGTCGCCGTGTGGAG GAACTATGCC
GATAACCGTG GTATAGTACGCTTGCACGTG CCCGTACATGCGTTGTAA
TG-3'

First Probe-11:
5'(phosphorylated)-TGGCGTAGGCAAGAGTGCCT GAACTATGCC
GATAACCGTG GTATAGTACGCTTGCACGTG CCCGTACATGCGTTGTAA
TG-3'

First Probe-12
5'(phosphorylated)-AGAGGAGTACAGTGCAATGA GAACTATGCC
GATAACCGTG GTATAGTACGCTTGCACGTG CCCGTACATGCGTTGTAA
TG-3'
```

(3) Target Genes

```
Target Gene-3 (the 3' side region is complementary
to CP-3-T):
5'-GGCCTGGTACACTGCCAGGC ACTTCTGCAGGTCATCGGCAT-3'

Target Gene-6 (the 3' side region is complementary
to CP-6-A)
5'-CATTCTAGCTAGTTCAACTT TCATTGCCATTTCAGCCAGCA-3'

Target Gene-7 (the 3' side region is complementary
to CP-7-G):
5'-TGCTCGCTTCCGCATACCCT CCTGCTGTAGTACCCAGAACA-3'

Target Gene-9 (the 3' side region is complementary
to CP-9-G):
5'-CTGCTGGTGCAGGGGCCACG CGGGGAGCAGCCTCTGGCATT-3'

Target Gene-10 (the 3' side region is complement-
ary to CP-10-C):
5'-CTCCACACGGCGACTCTCAT GATCATAGAACACGAACAGCT-3'

Target Gene 12 (the 3' side region is complement-
ary to CP-12-T):
5'-TCATTGCACTGTACTCCTCT AGACCTGCTGTGTCGAGAATA-3'
```

(4) HCP

```
HCP-2-1:
5'(Cy3 label)-GAACTATGCCGATAACCGTG GTATAGTACGCTTGC
ACGTG CCCGTACATGCGTTGTAATG-3'

HCP-2-2:
5'(Cy3 label)-CACGGTTATCGGCATAGTTC CACGTGCAAGCGTAC
TATAC CATTACAACGCATGTACGGG-3'
```

The capture probes, the 3' side regions of the first probes and the target genes were synthesized, respectively, based on the base sequences of the following genes.

Hemochromatosis gene: CP-1 and First Probe-1 (mutation site: 845th base), and CP-10, First Probe-10 and Target Gene-10 (mutation site: 187th base); Apolipoprotein E gene: CP-2 and First Probe-2 (mutation site: 112th amino acid residue), and CP-3, First Probe-3 and Target Gene-3 (mutation site: 158th amino acid residue); Apolipoprotein B100 gene: CP-4 and First Probe-4; Methylenetetrahydrofolate reductase gene: CP-5 and First Probe-5; Medium Chain Acyl-Coenzyme A Dehydrogenase gene: CP-6, First Probe-6 and Target Gene-6; Angiotensinogen gene: CP-7, First Probe-7 and Target Gene-7; p53 gene: CP-8 and First Probe-8 (mutation site: 47th amino acid residue), and CP-9, First Probe-9 and Target Gene-9 (mutation site: 72nd amino acid residue); and KRAS gene: CP-11 and First Probe-11 (mutation site: 12th amino acid residue), and CP-12 and First Probe-12 (mutation site: 61st amino acid residue).

The hybridization solution, the slide glass and the spotter used were the same as used in Example 1.

3. Methods 3-1. Preparation of Slide Glass

Each capture probe (CP 100 pmol/μL) and a spotting solution (manufactured by Matsunami Glass Ind., Ltd.) were mixed by the same amounts so that 24 types of probe solutions were prepared. The resulting probe solutions were spotted on the slide glass with respect to 12 genes to form 24 spots in the manner of N=1. When spotting another probe solution, the pins were washed with sterilized water and cold ethanol, and then air-dried. The spotted slide glass was placed in a wetting box and left overnight while shielded from light.

Thereafter, the capture probes were immobilized using the same procedure as in Example 1 so that a slide glass was finished.

3-2. Detection

Each of the six types of the target genes was added at a concentration of 30 pmol (30 μL) to the hybridization solution, and each of the 12 types of the first probes was also added at a concentration of 30 pmol (30 μL). Each solution (25 μL) was subjected to thermal dissociation at 95° C. for 2 minutes and then reacted in a chamber on the slide glass immobilized the 24 capture probes at 42° C. for 2 hours to hybridize each capture probe, each target gene and the first probe. After the reaction, the slide glass was washed twice with a 2×SSC and 0.1% SDS solution, once with a 1×SSC solution and once with a 0.2×SSC solution and then air-dried.

Thereafter, a ligation reaction, an alkali treatment and a self-assembly substance forming reaction were performed using the process of Example 1 except that HCP-2-1 and HCP-2-2 were used as the HCPs, and the fluorescence on the slide glass was observed with a fluorescence microscope. The result is shown in FIG. 28.

Figure 28:
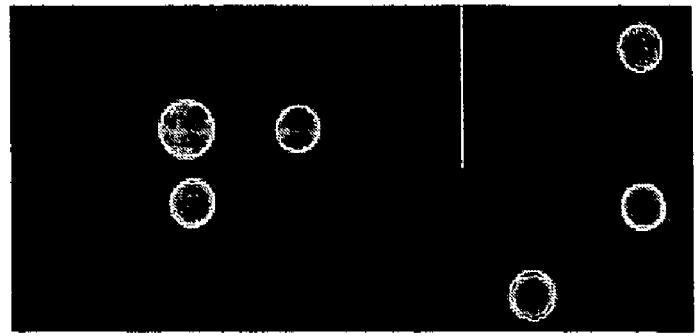
FIG. 28 is a photograph showing the result of Example 2.

FIG. 28 indicates that signal was amplified only when the mutation site of the target gene was complementary to the capture probe.

CAPABILITY OF EXPLOITATION IN INDUSTRY

As described above, according to the present invention, there is provided a signal amplification method for detecting mutated genes, which can increase the detection sensitivity of mutated genes on a DNA chip according to the PALSAR method, can establish efficient signal amplification and can establish simple detection by contriving design of oligonucleotide probes for use in the PALSAR method.

The invention claimed is:

1. A signal amplification method for detecting a mutated gene, comprising:
    a first step for hybridizing a capture probe and a first probe to a target DNA;
    a second step for joining the capture probe and the first probe by a ligation reaction with a DNA ligase when the target DNA has a mutation site that is complementary to the capture probe;
    a third step for removing the target DNA;
    a fourth step for adding a plurality of pairs of oligonucleotide probes to form a self-assembly substance by a self-assembly reaction of the oligonucleotide probes so that signal amplification is achieved; and
    a fifth step for conducting detection of the mutated gene by detecting the presence of the self-assembly substance,
    wherein the base sequences of the capture probe and the first probe are constructed such that, in the first step, the capture probe and the first probe are annealed to the target DNA in the state where an end of the capture probe hybridizes at the mutation site of the target DNA and the end is adjacent to the first probe, and
    at least one of the plurality of oligonucleotide probes has a region complementary to the first probe,
    wherein the self-assembly reaction comprises the steps of:
    providing the plurality of pairs of oligonucleotide probes comprising n (n≧3) regions, each region of one probe of the pair of oligonucleotide probes being complementary to a corresponding region of the other probe of the pair of oligonucleotide probes; and
    hybridizing the pairs of oligonucleotide probes such that the one probes and the other probes of the pairs of oligonucleotide probes cross each other in alternation,
    wherein the oligonucleotide probes are self-assembled to form the double-stranded self-assembly substance.

2. The signal amplification method according to claim 1, wherein the target DNA is single-stranded DNA or double-stranded DNA.

3. The signal amplification method according to claim 1, wherein a base sequence of the oligonucleotide for use in the self-assembly reaction is made previously complementary to a base sequence of the first probe.

4. The signal amplification method according to claim 1, wherein the capture probe is bound to a support.

5. The signal amplification method according to claim 4, wherein the support is a microplate type, a slide glass type, a particle type, or an electroconductive substrate type.

6. The signal amplification method according to claim 1, further comprising hybridizing a labeled probe with the self-assembly substance to detect the presence of the self-assembly substance.

7. The signal amplification method according to claim 6, wherein the labeled probe is a probe labeled with an enzyme of color generation type, an enzyme of luminescence generation type, or a radioisotope.

8. The signal amplification method according to claim 1, wherein the presence of the self-assembly substance is detected by:
    adding a fluorescent substance capable of binding to a nucleic acid to the self-assembly substance; and
    measuring a photochemical change of the fluorescent substance.

9. The signal amplification method according to claim 1, wherein the presence of the self-assembly substance is detected by:
    labeling previously the oligonucleotide for forming the self-assembly substance with a fluorescent substance; and
    measuring a photochemical change of the fluorescent substance.

10. The signal amplification method according to claim 1, wherein the presence of the self-assembly substance is detected by:
    labeling in advance the oligonucleotide for forming the self-assembly substance with a radioisotope; and
    detecting the radioisotope.

11. The signal amplification method according to claim 1, wherein the presence of the self-assembly substance is detected by:
    labeling in advance the oligonucleotide for forming the self-assembly substance with an enzyme of color generation type or an enzyme of luminescence generation type; and
    measuring a photochemical change due to the enzyme.

12. The signal amplification method according to claim 1, wherein the oligonucleotides are comprised of at least one base selected from the group consisting of DNA, RNA, PNA, and LNA.

* * * * *

SEQUENCE LISTING

```
<160> NUMBER OF SEQ ID NOS: 53

<210> SEQ ID NO 1
<211> LENGTH: 23
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: amino group attached at the 5' end

<400> SEQUENCE: 1
ggggaagagc agagatatac gta                                          23

<210> SEQ ID NO 2
<211> LENGTH: 23
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: amino group attached at the 5' end

<400> SEQUENCE: 2
ggggaagagc agagatatac gtt                                          23

<210> SEQ ID NO 3
<211> LENGTH: 23
<212> TYPE: DNA
```

```
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: amino group attached at the 5' end

<400> SEQUENCE: 3
ggggaagagc agagatatac gtg                                             23

<210> SEQ ID NO 4
<211> LENGTH: 23
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: amino group attached at the 5' end

<400> SEQUENCE: 4
ggggaagagc agagatatac gtc                                             23

<210> SEQ ID NO 5
<211> LENGTH: 41
<212> TYPE: DNA
<213> ORGANISM: Artificial
<220> FEATURE:
<223> OTHER INFORMATION: Synthetic Construct

<400> SEQUENCE: 5
ggcctgggtg ctccacctgg tacgtatatc tctgctcttc c                         41

<210> SEQ ID NO 6
<211> LENGTH: 41
<212> TYPE: DNA
<213> ORGANISM: Artificial
<220> FEATURE:
<223> OTHER INFORMATION: Synthetic Construct

<400> SEQUENCE: 6
ggcctgggtg ctccacctgg aacgtatatc tctgctcttc c                         41

<210> SEQ ID NO 7
<211> LENGTH: 41
<212> TYPE: DNA
<213> ORGANISM: Artificial
<220> FEATURE:
<223> OTHER INFORMATION: Synthetic Construct

<400> SEQUENCE: 7
ggcctgggtg ctccacctgg cacgtatatc tctgctcttc c                         41

<210> SEQ ID NO 8
<211> LENGTH: 41
<212> TYPE: DNA
<213> ORGANISM: Artificial
<220> FEATURE:
<223> OTHER INFORMATION: Synthetic Construct

<400> SEQUENCE: 8
ggcctgggtg ctccacctgg gacgtatatc tctgctcttc c                         41

<210> SEQ ID NO 9
<211> LENGTH: 48
```

```
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: phosphate group attached at the 5' end

<400> SEQUENCE: 9
ccaggtggag cacccagcat atgtagcaga gcgtaagtca tgtccacc                48

<210> SEQ ID NO 10
<211> LENGTH: 48
<212> TYPE: DNA
<213> ORGANISM: Artificial
<220> FEATURE:
<223> OTHER INFORMATION: Synthetic Construct

<400> SEQUENCE: 10
ccaggtggag cacccagcat atgtagcaga gcgtaagtca tgtccacc                48

<210> SEQ ID NO 11
<211> LENGTH: 48
<212> TYPE: DNA
<213> ORGANISM: Artificial
<220> FEATURE:
<223> OTHER INFORMATION: Synthetic Construct

<400> SEQUENCE: 11
tgggtgctcc acctgggctc tgctacatat gcggtggaca tgacttac                48

<210> SEQ ID NO 12
<211> LENGTH: 21
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: amino group attached at the 5' end

<400> SEQUENCE: 12
gcgcggacat ggaggacgtg t                                             21

<210> SEQ ID NO 13
<211> LENGTH: 21
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: amino group attached at the 5' end

<400> SEQUENCE: 13
gcgcggacat ggaggacgtg c                                             21

<210> SEQ ID NO 14
<211> LENGTH: 21
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
```

<223> OTHER INFORMATION: amino group attached at the 5' end

<400> SEQUENCE: 14
atgccgatga cctgcagaag c                                          21

<210> SEQ ID NO 15
<211> LENGTH: 21
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: amino group attached at the 5' end

<400> SEQUENCE: 15
atgccgatga cctgcagaag t                                          21

<210> SEQ ID NO 16
<211> LENGTH: 21
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: amino group attached at the 5' end

<400> SEQUENCE: 16
cttgaattcc aagagcacac g                                          21

<210> SEQ ID NO 17
<211> LENGTH: 21
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: amino group attached at the 5' end

<400> SEQUENCE: 17
cttgaattcc aagagcacac a                                          21

<210> SEQ ID NO 18
<211> LENGTH: 21
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: amino group attached at the 5' end

<400> SEQUENCE: 18
ggagaaggtg tctgcgggag c                                          21

<210> SEQ ID NO 19
<211> LENGTH: 21
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: amino group attached at the 5' end

<400> SEQUENCE: 19
ggagaaggtg tctgcgggag t                                            21

<210> SEQ ID NO 20
<211> LENGTH: 21
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: amino group attached at the 5' end

<400> SEQUENCE: 20
tgctggctga aatggcaatg a                                            21

<210> SEQ ID NO 21
<211> LENGTH: 21
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: amino group attached at the 5' end

<400> SEQUENCE: 21
tgctggctga aatggcaatg g                                            21

<210> SEQ ID NO 22
<211> LENGTH: 21
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: amino group attached at the 5' end

<400> SEQUENCE: 22
tgttctgggt actacagcag a                                            21

<210> SEQ ID NO 23
<211> LENGTH: 21
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: amino group attached at the 5' end

<400> SEQUENCE: 23
tgttctgggt actacagcag g                                            21

<210> SEQ ID NO 24
<211> LENGTH: 21
<212> TYPE: DNA
<213> ORGANISM: Artificial
<220> FEATURE:
<223> OTHER INFORMATION: Synthetic Construct
<220> FEATURE:

```
<221> NAME/KEY: misc_feature
<222> LOCATION: (1)..(1)
<223> OTHER INFORMATION: amino group attached at the 5' end

<400> SEQUENCE: 24
tggatgattt gatgctgtcc c                                              21

<210> SEQ ID NO 25
<211> LENGTH: 21
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: amino group attached at the 5' end

<400> SEQUENCE: 25
tggatgattt gatgctgtcc t                                              21

<210> SEQ ID NO 26
<211> LENGTH: 21
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: amino group attached at the 5' end

<400> SEQUENCE: 26
aatgccagag gctgctcccc g                                              21

<210> SEQ ID NO 27
<211> LENGTH: 21
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: amino group attached at the 5' end

<400> SEQUENCE: 27
aatgccagag gctgctcccc c                                              21

<210> SEQ ID NO 28
<211> LENGTH: 21
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: amino group attached at the 5' end

<400> SEQUENCE: 28
agctgttcgt gttctatgat c                                              21

<210> SEQ ID NO 29
<211> LENGTH: 21
<212> TYPE: DNA
<213> ORGANISM: Artificial
<220> FEATURE:
<223> OTHER INFORMATION: Synthetic Construct
```

```
<220> FEATURE:
<221> NAME/KEY: misc_feature
<222> LOCATION: (1)..(1)
<223> OTHER INFORMATION: amino group attached at the 5' end

<400> SEQUENCE: 29
agctgttcgt gttctatgat g                                              21

<210> SEQ ID NO 30
<211> LENGTH: 21
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: amino group attached at the 5' end

<400> SEQUENCE: 30
acttgtggta gttggagctg g                                              21

<210> SEQ ID NO 31
<211> LENGTH: 21
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: amino group attached at the 5' end

<400> SEQUENCE: 31
acttgtggta gttggagctg t                                              21

<210> SEQ ID NO 32
<211> LENGTH: 21
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: amino group attached at the 5' end

<400> SEQUENCE: 32
tattctcgac acagcaggtc a                                              21

<210> SEQ ID NO 33
<211> LENGTH: 21
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: amino group attached at the 5' end

<400> SEQUENCE: 33
tattctcgac acagcaggtc t                                              21

<210> SEQ ID NO 34
<211> LENGTH: 80
<212> TYPE: DNA
<213> ORGANISM: Artificial
<220> FEATURE:
```

<223> OTHER INFORMATION: Synthetic Construct
<220> FEATURE:
<221> NAME/KEY: misc_feature
<222> LOCATION: (1)..(1)
<223> OTHER INFORMATION: phosphate group attached at the 5' end

<400> SEQUENCE: 34
ccaggtggag cacccaggcc gaactatgcc gataaccgtg gtatagtacg cttgcacgtg    60
cccgtacatg cgttgtaatg                                                80

<210> SEQ ID NO 35
<211> LENGTH: 80
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: phosphate group attached at the 5' end

<400> SEQUENCE: 35
gcggccgcct ggtgcagtac gaactatgcc gataaccgtg gtatagtacg cttgcacgtg    60
cccgtacatg cgttgtaatg                                                80

<210> SEQ ID NO 36
<211> LENGTH: 80
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: phosphate group attached at the 5' end

<400> SEQUENCE: 36
gcctggcagt gtaccaggcc gaactatgcc gataaccgtg gtatagtacg cttgcacgtg    60
cccgtacatg cgttgtaatg                                                80

<210> SEQ ID NO 37
<211> LENGTH: 80
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: phosphate group attached at the 5' end

<400> SEQUENCE: 37
gtcttcagtg aagctgcagg gaactatgcc gataaccgtg gtatagtacg cttgcacgtg    60
cccgtacatg cgttgtaatg                                                80

<210> SEQ ID NO 38
<211> LENGTH: 80
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: phosphate group attached at the 5' end

<400> SEQUENCE: 38

```
cgatttcatc atcacgcagc gaactatgcc gataaccgtg gtatagtacg cttgcacgtg      60
cccgtacatg cgttgtaatg                                                 80
```

<210> SEQ ID NO 39
<211> LENGTH: 80
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: phosphate group attached at the 5' end

<400> SEQUENCE: 39

```
aagttgaact agctagaatg gaactatgcc gataaccgtg gtatagtacg cttgcacgtg      60
cccgtacatg cgttgtaatg                                                 80
```

<210> SEQ ID NO 40
<211> LENGTH: 80
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: phosphate group attached at the 5' end

<400> SEQUENCE: 40

```
agggtatgcg gaagcgagca gaactatgcc gataaccgtg gtatagtacg cttgcacgtg      60
cccgtacatg cgttgtaatg                                                 80
```

<210> SEQ ID NO 41
<211> LENGTH: 80
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: phosphate group attached at the 5' end

<400> SEQUENCE: 41

```
cggacgatat tgaacaatgg gaactatgcc gataaccgtg gtatagtacg cttgcacgtg      60
cccgtacatg cgttgtaatg                                                 80
```

<210> SEQ ID NO 42
<211> LENGTH: 80
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: phosphate group attached at the 5' end

<400> SEQUENCE: 42

```
cgtggcccct gcaccagcag gaactatgcc gataaccgtg gtatagtacg cttgcacgtg      60
cccgtacatg cgttgtaatg                                                 80
```

<210> SEQ ID NO 43

```
<211> LENGTH: 80
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: phosphate group attached at the 5' end

<400> SEQUENCE: 43
atgagagtcg ccgtgtggag gaactatgcc gataaccgtg gtatagtacg cttgcacgtg    60
cccgtacatg cgttgtaatg                                                80

<210> SEQ ID NO 44
<211> LENGTH: 80
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: phosphate group attached at the 5' end

<400> SEQUENCE: 44
tggcgtaggc aagagtgcct gaactatgcc gataaccgtg gtatagtacg cttgcacgtg    60
cccgtacatg cgttgtaatg                                                80

<210> SEQ ID NO 45
<211> LENGTH: 80
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: phosphate group attached at the 5' end

<400> SEQUENCE: 45
agaggagtac agtgcaatga gaactatgcc gataaccgtg gtatagtacg cttgcacgtg    60
cccgtacatg cgttgtaatg                                                80

<210> SEQ ID NO 46
<211> LENGTH: 41
<212> TYPE: DNA
<213> ORGANISM: Artificial
<220> FEATURE:
<223> OTHER INFORMATION: Synthetic Construct

<400> SEQUENCE: 46
ggcctggtac actgccaggc acttctgcag gtcatcggca t                        41

<210> SEQ ID NO 47
<211> LENGTH: 41
<212> TYPE: DNA
<213> ORGANISM: Artificial
<220> FEATURE:
<223> OTHER INFORMATION: Synthetic Construct

<400> SEQUENCE: 47
cattctagct agttcaactt tcattgccat ttcagccagc a                        41

<210> SEQ ID NO 48
<211> LENGTH: 41
```

-continued

<212> TYPE: DNA
<213> ORGANISM: Artificial
<220> FEATURE:
<223> OTHER INFORMATION: Synthetic Construct

<400> SEQUENCE: 48
tgctcgcttc cgcataccct cctgctgtag tacccagaac a             41

<210> SEQ ID NO 49
<211> LENGTH: 41
<212> TYPE: DNA
<213> ORGANISM: Artificial
<220> FEATURE:
<223> OTHER INFORMATION: Synthetic Construct

<400> SEQUENCE: 49
ctgctggtgc aggggccacg cggggagcag cctctggcat t             41

<210> SEQ ID NO 50
<211> LENGTH: 41
<212> TYPE: DNA
<213> ORGANISM: Artificial
<220> FEATURE:
<223> OTHER INFORMATION: Synthetic Construct

<400> SEQUENCE: 50
ctccacacgg cgactctcat gatcatagaa cacgaacagc t             41

<210> SEQ ID NO 51
<211> LENGTH: 41
<212> TYPE: DNA
<213> ORGANISM: Artificial
<220> FEATURE:
<223> OTHER INFORMATION: Synthetic Construct

<400> SEQUENCE: 51
tcattgcact gtactcctct agacctgctg tgtcgagaat a             41

<210> SEQ ID NO 52
<211> LENGTH: 60
<212> TYPE: DNA
<213> ORGANISM: Artificial
<220> FEATURE:
<223> OTHER INFORMATION: Synthetic Construct

<400> SEQUENCE: 52
gaactatgcc gataaccgtg gtatagtacg cttgcacgtg cccgtacatg cgttgtaatg    60

<210> SEQ ID NO 53
<211> LENGTH: 60
<212> TYPE: DNA
<213> ORGANISM: Artificial
<220> FEATURE:
<223> OTHER INFORMATION: Synthetic Construct

<400> SEQUENCE: 53
cacggttatc ggcatagttc cacgtgcaag cgtactatac cattacaacg catgtacggg    60